US008691237B2

(12) United States Patent
Andrews et al.

(10) Patent No.: US 8,691,237 B2

(45) Date of Patent: Apr. 8, 2014

(54) ***BRUCELLA ABORTUS* PROTEINS AND METHODS OF USE THEREOF**

(75) Inventors: Gerard P. Andrews, Laramie, WY (US); John E. Lowry, Fort Collins, CO (US)

(73) Assignee: The University of Wyoming, Laramie, WY (US)

( * ) Notice: Subject to any disclaimer, the term of this patent is extended or adjusted under 35 U.S.C. 154(b) by 161 days.

(21) Appl. No.: 12/959,881

(22) Filed: Dec. 3, 2010

(65) Prior Publication Data

US 2011/0177127 A1 Jul. 21, 2011

Related U.S. Application Data

(60) Provisional application No. 61/267,361, filed on Dec. 7, 2009.

(51) Int. Cl.

| | |
|---|---|
| ***A61K 39/00*** | (2006.01) |
| ***A61K 39/02*** | (2006.01) |
| ***C07K 1/00*** | (2006.01) |

(52) U.S. Cl.

USPC .................. 424/185.1; 424/190.1; 424/234.1; 424/252.1; 530/350

(58) Field of Classification Search

None

See application file for complete search history.

(56) References Cited

U.S. PATENT DOCUMENTS

2007/0118916 A1 * 5/2007 Puzio et al. .................. 800/278

OTHER PUBLICATIONS

Brooks-Alder et al (Infection and Immunity vol. 56, No. 10, pp. 2581-2586, 1988).*

Lowry, J. E., "*Brucella abortus*, malate dehydrogenase (Mdh) modulates production of anti-inflammatory cytokines during infection." (2009) Poster at 90th Annual Meeting of the conference of Research Workers in Animal Disease; Dec. 6-8, 2009; Chicago, IL.

Lowry, J. E., et al. "Vacciantion with recombinant antigens reduces *Brucella abortus* strain 19 colonization in a mouse model for infection." (2008) Poster at 89th Annual Meeting of the Conference of Research Workers in Animal Disease; Dec. 7-9, 2008; Chicago, IL.

Andrews, Gerard P., et al. "Identification of in Vivo-Induced Conserved Sequences from *Yersinia pestis* During Experimental Plague Infection in the Rabbit," Vector-Borne and Zoonotic Diseases; (2010) vol. 10(8): 749-756.

Lowry, Jake E., et al. "Vaccination with *Brucella abortus* Recombinant in Vivo-Induced Antigens Reduces Bacterial Load and Promotes Clearance in a Mouse Model for Infection," PLoS ONE; Mar. 2011; vol. 6(3)e17425: 1-6.

Wang, Yufei, et al. "The type IV secretion system affects the expression of Omp25/Omp31 and the outer membrane properties of *Briucella melitensis*." Federation of European Microbiological Societies; Microbiology Letters; (2010): 303:92-100.

Spera, Juan Manuel, et al. "A B Lymphocyte mitogen is a *Breucella abortus* virulence factor required for persistent infection." PNAS; Oct. 31, 2006; 103(44): 16514-16519.

Ko, Junkyuung, et al. "Molecular Host-Pathogen Interaction in *Brucellois*: Current Understanding and Future Approaches to Vaccine Development for Mice and Humans" Clinical Microbiology Reviews; Jan. 2003, vol. 16(1): 65-78.

Liu, Dan, et al. "An O-Antigen Processing Function for Wzx (RfbX): a promising Candidate for O-Unit Flippase." Journal of Bacteriology; Apr. 1996; vol. 178(7): 2102-2107.

Roux, Christelle M., et al. "*Brucella* requires a functional type IV secretion system to elict innate immune responses in mice." Cellular Microbiology; (2007); 9(7): 1851-1869.

Comerci, Diego J., et al. Essential role of the VirB machinery in the maturation of the *Brucella abortus*-containing vacuole. Cellular Microbiology (2001) 3(3): 159-168.

Vines, Enrique D., et al. "Defective O-Antigen Polymerization in tolA and pal Mutants of *Escherichia coli* in Response to Extracytoplasmic Stress." Journal of Bacteriology, May 2005; vol. 187(10): 3359-3368.

Anderson, Eric S., et al. "The Manganese Transporter MntH Is a Critical Virulence Determinant for *Brucella abortus* 2308 in Experimentally Infected Mice." Infection and Immunity; Aug. 2009; vol. 77(8): 3466-3474.

Miranda, Regina L., et al. "Glycolytic and Gluconeogenic Growth of *Escherichia coli* O157:H7 (EDL933) and *E. coli* K-12 (MG 1655) in the Mouse Interstine." Infection and Immunity; Mar. 2004; vol. 72(3): 1666-1676.

Tang, Dong-Jie, et al. "*Xanthomonas campestris* pv. campestris Possesses a Single Gluconegenic Pathway That is Required for Virulence," Journal of Bacteriology, Sep. 2005; vol. 187(17): 6231-6237.

Caro-Hernandez, Paola, et al. "Role of the Omp25/Omp31 Family in Outer Membrane Properties and virulence of *Brucella ovis*." Infection and Immunity, Aug. 2007; vol. 75(8): 4050-4061.

Chirhart-Gilleland, Rebecca L, et al. "Identification and Characterization of a 14-Kilodalton *Brucella abortus* Protein Reactive with Antibodies from Naturally Experimentally Infected Hosts and T Lymphocytes from Experimentally Infected BALB/c Mice." Infection and Immunity, Aug. 1998; vol. 66(8): 4000-4003.

Robert, Viviane, et al. "Assembly Factor Omp85 Recognizes Its Outer Membrane Protein Substrates by a Species-Specific C-Terminal Motif" PLoS Biology, Nov. 2006; vol. 4(11)e377; 1984-1995.

Manning, D. Scott, et al. "Omp85 proteins of *Neisseria gonorrhoeae* and *Neisseria meningitdis* are similar to Haemophilus influenzae D-15-Ag and *Passteurella multocida* Oma87" Microbial Pathogenesis (1998) vol. 25: 11-21.

Lowry, J.E., et al. "Identification of *Brucella abortus* genes in elk (*Cervis elaphus*) using in vivo-induced antigen technology (IVIAT) revels novel markers of infection." Veterinary Microbiology (2010) 142: 367-372.

* cited by examiner

*Primary Examiner* — Albert Navarro

(74) *Attorney, Agent, or Firm* — Robert C. Netter, Jr.; Dann, Dorfman, Herrell & Skillman

(57) ABSTRACT

Compositions and methods for the diagnosis and prevention of *B. abortus* infection are provided.

8 Claims, 11 Drawing Sheets

Figure 1:
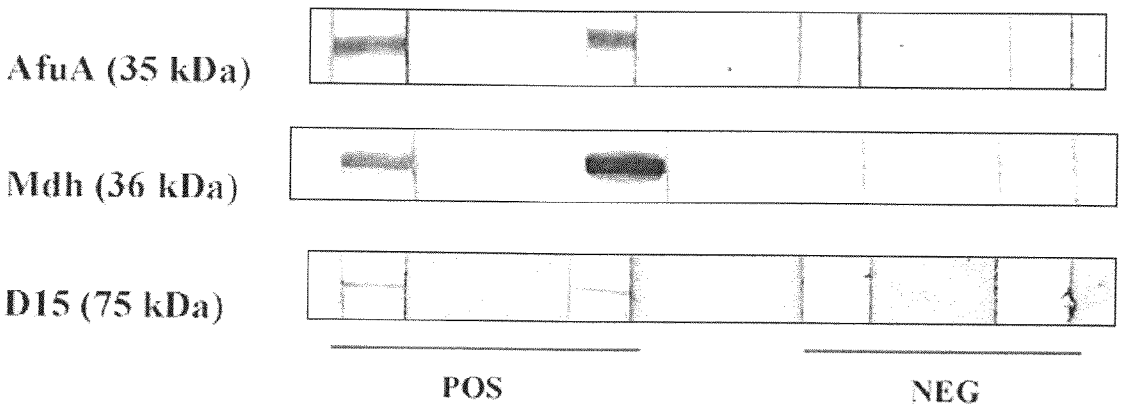

```
  1 mllltahfss falspalafe ifgihlwgkd kkqdpdiidp ktysvdvttt gdrknadgke
 61 adlksviega sglvsdadkp asgsagllak argdyrrils alygegrygg tisikvdgre
121 andippdtei pnnakvaitv dpgpqflfsr taisniappp gnrrdkvqtp eeagfapgqe
181 aksgtilkae rlaveawrqe gyakarvtge dvvadhadnr vsadialdpg rkayygpvsv
241 vgtarmdpqf vawmtglkpg qeydpddien akkrlgrmev framtfeead kiepdgslpi
301 tlnvqerkpr rfgfgaeyst idgfgvtsyw mhrnlfgrge rlrfdakvsg iggsqdnsfd
361 pknytyllga sfakpgvytp dtdfvatlda krevldayte tsinaktgft qifsdelsga
421 lyanasqghf vddvfgkrdf ttaglegnll ydsrnnkpdp ssgfylvgni qpfyefhygn
481 fatrftaegr tyhgfgqtdr vvlagrlkvg sivggsiadl ppsqlflagg ggsvrgygyr
541 nigvsagngn iiggrslvea ngevrtritd sigavafvda gyvgeksfpd fseqmrvgvg
601 gglryltslg pirldvavpl nrrsgdpnyg fyvgigqaf
```

Figure 2

```
  1 marnkialig sgmiggtlah laglkelgdv vlfdiaegtp qgkgldiaes spvdgfdakf
 61 tgandyaaie gadvvivtag vprkpgmsrd dllginlkvm eqvgagikky apeafvicit
121 npldamvwal qkfsglpahk vvgmagvlds arfryflsee fnvsvedvtv fvlgghgdsm
181 vplarystva giplpdlvkm gwtsqdkldk iiqrtrdgga eivgllktgs afyapaasai
241 qmaesylkdk krvlpvaaql sgqygvkdmy vgvptvigan gveriieidl dkdekaqfdk
301 svasvaglce acigiapslk
```

Figure 3

```
  1 msiiarsala lvavtlvtga ahadevnlyt trepgliqpl ldafksstgi tvntvflkdg
 61 laervasege nspadilmtv dagnlvdlkd kgltqpidsk vlkeavpaql rdadgdwyal
121 smrarvvyad kdmeidkity eelsdpkwkg kiciragqhp yntalfadyi ahhgvaktee
181 wlaglkanla rkaaggdrdg akdivggicd lavansyyvg lmrsgkgged qkvwgegikv
241 llptfqgggt qvnisgaava khaphkeeav klleylvsde aqqqiyakan yeypvkpgap
301 ldpivesfge lkidtvplse ivshrkqase lvdkvgfdn
```

Figure 4

```
  1 mtvfgidaah lnirhvadga vtatstdavn grqlfavseq aasgwsltvn gmdksrvapg
 61 dmvdlsnsdg nlvlskhgtg vtfnlapdlk vtslvagntf ldtnglvitg gpsmtvfgid
121 aahlnirhva dgavtatstd avngrqlfav seqaasgwsl tvngmdksrv apgdmvdlsn
181 sdgnlvlskh gtgvtfnlap dlkvtslvag ntfldtnglv itggpsmtvs gidaghlnir
241 hvadgavtat stdavngrql favseqaasg wsltvngmdk srvgpgdtvd lsnsdgnlvl
301 skhgtgvtfn lapdlkvtsl vagntfldtn glvitggpsm tvsgidagql kishvadgav
361 tvtstdavng sqlhrvahti aehlggdahv nadgsvigpq ytvqkkrykt iydafggvde
421 nlsnindilh diesgggiky fhansigads ralgtnsiav gsdsvasgeg sisvgngaqa
481 sahgsvalge naaapdansv algagsktse vvatkgttin gqyydfagda psgtvsvgdk
541 gaertitnva agrisvestd avngsqlnav nqaienlaag vtendkfsvk ydrhsdgtkk
601 nsmtlqgwds atpvvlanva dgvhkndavn vsqlkaglst tlgeakaytd qtalqtldqa
661 naytdkkfgk lnedivatri earqaaaigl aaaslryddr pgkisaaigg gfwrgegava
721 lglghtsedq rmrsnlsaat sggnwgmgag fsytfn
```

Figure 11

SEQUENCE LISTING

```
<160> NUMBER OF SEQ ID NOS: 5

<210> SEQ ID NO 1
<211> LENGTH: 639
<212> TYPE: PRT
<213> ORGANISM: Brucella abortus

<400> SEQUENCE: 1

Met Leu Leu Leu Thr Ala His Phe Ser Ser Phe Ala Leu Ser Pro Ala
1               5                   10                  15

Leu Ala Phe Glu Ile Phe Gly Ile His Leu Trp Gly Lys Asp Lys Lys
            20                  25                  30

Gln Asp Pro Asp Ile Ile Asp Pro Lys Thr Tyr Ser Val Asp Val Thr
        35                  40                  45

Thr Thr Gly Asp Arg Lys Asn Ala Asp Gly Lys Glu Ala Asp Leu Lys
    50                  55                  60

Ser Val Ile Glu Gly Ala Ser Gly Leu Val Ser Asp Ala Asp Lys Pro
65                  70                  75                  80

Ala Ser Gly Ser Ala Gly Leu Leu Ala Lys Ala Arg Gly Asp Tyr Arg
                85                  90                  95

Arg Ile Leu Ser Ala Leu Tyr Gly Glu Gly Arg Tyr Gly Gly Thr Ile
            100                 105                 110

Ser Ile Lys Val Asp Gly Arg Glu Ala Asn Asp Ile Pro Pro Asp Thr
        115                 120                 125

Glu Ile Pro Asn Asn Ala Lys Val Ala Ile Thr Val Asp Pro Gly Pro
    130                 135                 140

Gln Phe Leu Phe Ser Arg Thr Ala Ile Ser Asn Ile Ala Pro Pro Pro
145                 150                 155                 160

Gly Asn Arg Arg Asp Lys Val Gln Thr Pro Glu Glu Ala Gly Phe Ala
                165                 170                 175

Pro Gly Gln Glu Ala Lys Ser Gly Thr Ile Leu Lys Ala Glu Arg Leu
            180                 185                 190

Ala Val Glu Ala Trp Arg Gln Glu Gly Tyr Ala Lys Ala Arg Val Thr
        195                 200                 205
```

-continued

```
Gly Glu Asp Val Val Ala Asp His Ala Asp Asn Arg Val Ser Ala Asp
    210                 215                 220

Ile Ala Leu Asp Pro Gly Arg Lys Ala Tyr Tyr Gly Pro Val Ser Val
225                 230                 235                 240

Val Gly Thr Ala Arg Met Asp Pro Gln Phe Val Ala Trp Met Thr Gly
                245                 250                 255

Leu Lys Pro Gly Gln Glu Tyr Asp Pro Asp Asp Ile Glu Asn Ala Lys
            260                 265                 270

Lys Arg Leu Gly Arg Met Glu Val Phe Arg Ala Met Thr Phe Glu Glu
        275                 280                 285

Ala Asp Lys Ile Glu Pro Asp Gly Ser Leu Pro Ile Thr Leu Asn Val
    290                 295                 300

Gln Glu Arg Lys Pro Arg Arg Phe Gly Phe Gly Ala Glu Tyr Ser Thr
305                 310                 315                 320

Ile Asp Gly Phe Gly Val Thr Ser Tyr Trp Met His Arg Asn Leu Phe
                325                 330                 335

Gly Arg Gly Glu Arg Leu Arg Phe Asp Ala Lys Val Ser Gly Ile Gly
            340                 345                 350

Gly Ser Gln Asp Asn Ser Phe Asp Pro Lys Asn Tyr Thr Tyr Leu Leu
        355                 360                 365

Gly Ala Ser Phe Ala Lys Pro Gly Val Tyr Thr Pro Asp Thr Asp Phe
    370                 375                 380

Val Ala Thr Leu Asp Ala Lys Arg Glu Val Leu Asp Ala Tyr Thr Glu
385                 390                 395                 400

Thr Ser Ile Asn Ala Lys Thr Gly Phe Thr Gln Ile Phe Ser Asp Glu
                405                 410                 415

Leu Ser Gly Ala Leu Tyr Ala Asn Ala Ser Gln Gly His Phe Val Asp
            420                 425                 430

Asp Val Phe Gly Lys Arg Asp Phe Thr Thr Ala Gly Leu Glu Gly Asn
        435                 440                 445

Leu Leu Tyr Asp Ser Arg Asn Asn Lys Pro Asp Pro Ser Ser Gly Phe
    450                 455                 460

Tyr Leu Val Gly Asn Ile Gln Pro Phe Tyr Glu Phe His Tyr Gly Asn
465                 470                 475                 480

Phe Ala Thr Arg Phe Thr Ala Glu Gly Arg Thr Tyr His Gly Phe Gly
                485                 490                 495

Gln Thr Asp Arg Val Val Leu Ala Gly Arg Leu Lys Val Gly Ser Ile
            500                 505                 510

Val Gly Gly Ser Ile Ala Asp Leu Pro Pro Ser Gln Leu Phe Leu Ala
        515                 520                 525

Gly Gly Gly Gly Ser Val Arg Gly Tyr Gly Tyr Arg Asn Ile Gly Val
    530                 535                 540

Ser Ala Gly Asn Gly Asn Ile Ile Gly Gly Arg Ser Leu Val Glu Ala
545                 550                 555                 560

Asn Gly Glu Val Arg Thr Arg Ile Thr Asp Ser Ile Gly Ala Val Ala
                565                 570                 575

Phe Val Asp Ala Gly Tyr Val Gly Glu Lys Ser Phe Pro Asp Phe Ser
            580                 585                 590

Glu Gln Met Arg Val Gly Val Gly Gly Gly Leu Arg Tyr Leu Thr Ser
        595                 600                 605

Leu Gly Pro Ile Arg Leu Asp Val Ala Val Pro Leu Asn Arg Arg Ser
    610                 615                 620

Gly Asp Pro Asn Tyr Gly Phe Tyr Val Gly Ile Gly Gln Ala Phe
625                 630                 635
```

-continued

<210> SEQ ID NO 2
<211> LENGTH: 320
<212> TYPE: PRT
<213> ORGANISM: Brucella abortus

<400> SEQUENCE: 2

```
Met Ala Arg Asn Lys Ile Ala Leu Ile Gly Ser Gly Met Ile Gly Gly
 1               5                  10                  15

Thr Leu Ala His Leu Ala Gly Leu Lys Glu Leu Gly Asp Val Val Leu
            20                  25                  30

Phe Asp Ile Ala Glu Gly Thr Pro Gln Gly Lys Gly Leu Asp Ile Ala
        35                  40                  45

Glu Ser Ser Pro Val Asp Gly Phe Asp Ala Lys Phe Thr Gly Ala Asn
    50                  55                  60

Asp Tyr Ala Ala Ile Glu Gly Ala Asp Val Val Ile Val Thr Ala Gly
65                  70                  75                  80

Val Pro Arg Lys Pro Gly Met Ser Arg Asp Asp Leu Leu Gly Ile Asn
                85                  90                  95

Leu Lys Val Met Glu Gln Val Gly Ala Gly Ile Lys Lys Tyr Ala Pro
            100                 105                 110

Glu Ala Phe Val Ile Cys Ile Thr Asn Pro Leu Asp Ala Met Val Trp
        115                 120                 125

Ala Leu Gln Lys Phe Ser Gly Leu Pro Ala His Lys Val Val Gly Met
    130                 135                 140

Ala Gly Val Leu Asp Ser Ala Arg Phe Arg Tyr Phe Leu Ser Glu Glu
145                 150                 155                 160

Phe Asn Val Ser Val Glu Asp Val Thr Val Phe Val Leu Gly Gly His
                165                 170                 175

Gly Asp Ser Met Val Pro Leu Ala Arg Tyr Ser Thr Val Ala Gly Ile
            180                 185                 190

Pro Leu Pro Asp Leu Val Lys Met Gly Trp Thr Ser Gln Asp Lys Leu
        195                 200                 205

Asp Lys Ile Ile Gln Arg Thr Arg Asp Gly Gly Ala Glu Ile Val Gly
    210                 215                 220

Leu Leu Lys Thr Gly Ser Ala Phe Tyr Ala Pro Ala Ala Ser Ala Ile
225                 230                 235                 240

Gln Met Ala Glu Ser Tyr Leu Lys Asp Lys Lys Arg Val Leu Pro Val
                245                 250                 255

Ala Ala Gln Leu Ser Gly Gln Tyr Gly Val Lys Asp Met Tyr Val Gly
            260                 265                 270

Val Pro Thr Val Ile Gly Ala Asn Gly Val Glu Arg Ile Ile Glu Ile
        275                 280                 285

Asp Leu Asp Lys Asp Glu Lys Ala Gln Phe Asp Lys Ser Val Ala Ser
    290                 295                 300

Val Ala Gly Leu Cys Glu Ala Cys Ile Gly Ile Ala Pro Ser Leu Lys
305                 310                 315                 320
```

<210> SEQ ID NO 3
<211> LENGTH: 339
<212> TYPE: PRT
<213> ORGANISM: Brucella abortus

<400> SEQUENCE: 3

```
Met Ser Ile Ile Ala Arg Ser Ala Leu Ala Leu Val Ala Val Thr Leu
 1               5                  10                  15
```

Val Thr Gly Ala Ala His Ala Asp Glu Val Asn Leu Tyr Thr Thr Arg
20 25 30

Glu Pro Gly Leu Ile Gln Pro Leu Leu Asp Ala Phe Lys Ser Ser Thr
35 40 45

Gly Ile Thr Val Asn Thr Val Phe Leu Lys Asp Gly Leu Ala Glu Arg
50 55 60

Val Ala Ser Glu Gly Glu Asn Ser Pro Ala Asp Ile Leu Met Thr Val
65 70 75 80

Asp Ala Gly Asn Leu Val Asp Leu Lys Asp Lys Gly Leu Thr Gln Pro
85 90 95

Ile Asp Ser Lys Val Leu Lys Glu Ala Val Pro Ala Gln Leu Arg Asp
100 105 110

Ala Asp Gly Asp Trp Tyr Ala Leu Ser Met Arg Ala Arg Val Val Tyr
115 120 125

Ala Asp Lys Asp Met Glu Ile Asp Lys Ile Thr Tyr Glu Glu Leu Ser
130 135 140

Asp Pro Lys Trp Lys Gly Lys Ile Cys Ile Arg Ala Gly Gln His Pro
145 150 155 160

Tyr Asn Thr Ala Leu Phe Ala Asp Tyr Ile Ala His His Gly Val Ala
165 170 175

Lys Thr Glu Glu Trp Leu Ala Gly Leu Lys Ala Asn Leu Ala Arg Lys
180 185 190

Ala Ala Gly Gly Asp Arg Asp Gly Ala Lys Asp Ile Val Gly Gly Ile
195 200 205

Cys Asp Leu Ala Val Ala Asn Ser Tyr Tyr Val Gly Leu Met Arg Ser
210 215 220

Gly Lys Gly Gly Glu Asp Gln Lys Val Trp Gly Glu Gly Ile Lys Val
225 230 235 240

Leu Leu Pro Thr Phe Gln Gly Gly Gly Thr Gln Val Asn Ile Ser Gly
245 250 255

Ala Ala Val Ala Lys His Ala Pro His Lys Glu Glu Ala Val Lys Leu
260 265 270

Leu Glu Tyr Leu Val Ser Asp Glu Ala Gln Gln Gln Ile Tyr Ala Lys
275 280 285

Ala Asn Tyr Glu Tyr Pro Val Lys Pro Gly Ala Pro Leu Asp Pro Ile
290 295 300

Val Glu Ser Phe Gly Glu Leu Lys Ile Asp Thr Val Pro Leu Ser Glu
305 310 315 320

Ile Val Ser His Arg Lys Gln Ala Ser Glu Leu Val Asp Lys Val Gly
325 330 335

Phe Asp Asn

<210> SEQ ID NO 4
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 4

Met Ala His His His His His His Val Asp Asp Asp Asp Lys
1 5 10

<210> SEQ ID NO 5
<211> LENGTH: 756
<212> TYPE: PRT
<213> ORGANISM: Brucella Abortus -continued

<400> SEQUENCE: 5

```
Met Thr Val Phe Gly Ile Asp Ala Ala His Leu Asn Ile Arg His Val
1               5                   10                  15

Ala Asp Gly Ala Val Thr Ala Thr Ser Thr Asp Ala Val Asn Gly Arg
            20                  25                  30

Gln Leu Phe Ala Val Ser Glu Gln Ala Ala Ser Gly Trp Ser Leu Thr
        35                  40                  45

Val Asn Gly Met Asp Lys Ser Arg Val Ala Pro Gly Asp Met Val Asp
    50                  55                  60

Leu Ser Asn Ser Asp Gly Asn Leu Val Leu Ser Lys His Gly Thr Gly
65                  70                  75                  80

Val Thr Phe Asn Leu Ala Pro Asp Leu Lys Val Thr Ser Leu Val Ala
                85                  90                  95

Gly Asn Thr Phe Leu Asp Thr Asn Gly Leu Val Ile Thr Gly Gly Pro
            100                 105                 110

Ser Met Thr Val Phe Gly Ile Asp Ala Ala His Leu Asn Ile Arg His
        115                 120                 125

Val Ala Asp Gly Ala Val Thr Ala Thr Ser Thr Asp Ala Val Asn Gly
    130                 135                 140

Arg Gln Leu Phe Ala Val Ser Glu Gln Ala Ala Ser Gly Trp Ser Leu
145                 150                 155                 160

Thr Val Asn Gly Met Asp Lys Ser Arg Val Ala Pro Gly Asp Met Val
                165                 170                 175

Asp Leu Ser Asn Ser Asp Gly Asn Leu Val Leu Ser Lys His Gly Thr
            180                 185                 190

Gly Val Thr Phe Asn Leu Ala Pro Asp Leu Lys Val Thr Ser Leu Val
        195                 200                 205

Ala Gly Asn Thr Phe Leu Asp Thr Asn Gly Leu Val Ile Thr Gly Gly
    210                 215                 220

Pro Ser Met Thr Val Ser Gly Ile Asp Ala Gly His Leu Asn Ile Arg
225                 230                 235                 240

His Val Ala Asp Gly Ala Val Thr Ala Thr Ser Thr Asp Ala Val Asn
                245                 250                 255

Gly Arg Gln Leu Phe Ala Val Ser Glu Gln Ala Ala Ser Gly Trp Ser
            260                 265                 270

Leu Thr Val Asn Gly Met Asp Lys Ser Arg Val Gly Pro Gly Asp Thr
        275                 280                 285

Val Asp Leu Ser Asn Ser Asp Gly Asn Leu Val Leu Ser Lys His Gly
    290                 295                 300

Thr Gly Val Thr Phe Asn Leu Ala Pro Asp Leu Lys Val Thr Ser Leu
305                 310                 315                 320

Val Ala Gly Asn Thr Phe Leu Asp Thr Asn Gly Leu Val Ile Thr Gly
                325                 330                 335

Gly Pro Ser Met Thr Val Ser Gly Ile Asp Ala Gly Gln Leu Lys Ile
            340                 345                 350

Ser His Val Ala Asp Gly Ala Val Thr Val Thr Ser Thr Asp Ala Val
        355                 360                 365

Asn Gly Ser Gln Leu His Arg Val Ala His Thr Ile Ala Glu His Leu
    370                 375                 380

Gly Gly Asp Ala His Val Asn Ala Asp Gly Ser Val Ile Gly Pro Gln
385                 390                 395                 400

Tyr Thr Val Gln Lys Lys Arg Tyr Lys Thr Ile Tyr Asp Ala Phe Gly
                405                 410                 415
```

-continued

```
Gly Val Asp Glu Asn Leu Ser Asn Ile Asn Asp Ile Leu His Asp Ile
            420                 425                 430

Glu Ser Gly Gly Gly Ile Lys Tyr Phe His Ala Asn Ser Ile Gly Ala
        435                 440                 445

Asp Ser Arg Ala Leu Gly Thr Asn Ser Ile Ala Val Gly Ser Asp Ser
    450                 455                 460

Val Ala Ser Gly Glu Gly Ser Ile Ser Val Gly Asn Gly Ala Gln Ala
465                 470                 475                 480

Ser Ala His Gly Ser Val Ala Leu Gly Glu Asn Ala Ala Ala Pro Asp
                485                 490                 495

Ala Asn Ser Val Ala Leu Gly Ala Gly Ser Lys Thr Ser Glu Val Val
            500                 505                 510

Ala Thr Lys Gly Thr Thr Ile Asn Gly Gln Tyr Tyr Asp Phe Ala Gly
        515                 520                 525

Asp Ala Pro Ser Gly Thr Val Ser Val Gly Asp Lys Gly Ala Glu Arg
    530                 535                 540

Thr Ile Thr Asn Val Ala Ala Gly Arg Ile Ser Val Glu Ser Thr Asp
545                 550                 555                 560

Ala Val Asn Gly Ser Gln Leu Asn Ala Val Asn Gln Ala Ile Glu Asn
                565                 570                 575

Leu Ala Ala Gly Val Thr Glu Asn Asp Lys Phe Ser Val Lys Tyr Asp
            580                 585                 590

Arg His Ser Asp Gly Thr Lys Lys Asn Ser Met Thr Leu Gln Gly Trp
        595                 600                 605

Asp Ser Ala Thr Pro Val Val Leu Ala Asn Val Ala Asp Gly Val His
    610                 615                 620

Lys Asn Asp Ala Val Asn Val Ser Gln Leu Lys Ala Gly Leu Ser Thr
625                 630                 635                 640

Thr Leu Gly Glu Ala Lys Ala Tyr Thr Asp Gln Thr Ala Leu Gln Thr
                645                 650                 655

Leu Asp Gln Ala Asn Ala Tyr Thr Asp Lys Lys Phe Gly Lys Leu Asn
            660                 665                 670

Glu Asp Ile Val Ala Thr Arg Ile Glu Ala Arg Gln Ala Ala Ala Ile
        675                 680                 685

Gly Leu Ala Ala Ala Ser Leu Arg Tyr Asp Asp Arg Pro Gly Lys Ile
    690                 695                 700

Ser Ala Ala Ile Gly Gly Gly Phe Trp Arg Gly Glu Gly Ala Val Ala
705                 710                 715                 720

Leu Gly Leu Gly His Thr Ser Glu Asp Gln Arg Met Arg Ser Asn Leu
                725                 730                 735

Ser Ala Ala Thr Ser Gly Gly Asn Trp Gly Met Gly Ala Gly Phe Ser
            740                 745                 750

Tyr Thr Phe Asn
        755
```

*BRUCELLA ABORTUS* PROTEINS AND METHODS OF USE THEREOF

This application claims priority under 35 U.S.C. §119(e) to U.S. Provisional Patent Application No. 61/267,361, filed on Dec. 7, 2009. The foregoing application is incorporated by reference herein.

FIELD OF THE INVENTION

The present invention relates to the fields of diagnosing and preventing microbial infections. More specifically, the invention provides compositions for the detection of *Brucella abortus* and compositions to inhibit/vaccinate against *Brucella abortus* infections.

BACKGROUND OF THE INVENTION

The threat of brucellosis is of particular concern because of its potential to disrupt agricultural economy, and the disease continues to be problematic in parts of the U.S. today. To compound the problem, elk and wild bison within the Greater Yellowstone Area (GYA) are major reservoirs for brucellosis and cattle may contract *Brucella abortus* from this population (Godfroid, J. (2002) Rev. Sci. Technol. Off. Int. Epiz., 21:277-286). Wildlife *Brucella* reservoirs represent a major obstacle to the development of an effective eradication program focusing on domestic livestock in Wyoming. Therefore, the Wyoming Brucellosis Coordination Team has issued a series of management practices aimed at controlling brucellosis in elk. Among these practices is a recommendation to test feed ground elk as a way to monitor sero-prevalence and efficacy of brucellosis elimination activities.

Unfortunately, diagnostic methods for brucellosis have been limited because of the lack of consistently reliable targets which ensure high specificity and sensitivity. More sensitive than traditional *Brucella* diagnostic methods, serologic diagnosis based on reactivity to LPS has been reported (Saegerman et al. (2004) Vet. Microbiol., 100:91-105). Geographic areas of false positive serologic reactions exist however, which reduce specificity of such assays (Saegerman et al. (2004) Vet. Microbial., 100:91-105). More recently, PCR-based tests have been evaluated as a next-generation approach to early diagnosis/detection, although standardization of methodologies and a more diverse repertoire of target genes still need to be established (Al Dahouk et al. (2004) Clin. Lab., 50:387-394; Navarro et al. (2004) Exp. Rev. Mol. Diag., 4:115-123).

While several genes and their products associated with *Brucella* virulence have been described (for review, see Ko et al. (2003) Clin. Microbiol. Rev., 16:65-78), most have been identified using in vitro-grown bacteria. In this approach, host factors important in up-regulating some virulence loci may not be present in laboratory-grown cultures. Signature Tagged Mutagenesis (STM) has been employed with *Brucella* spp. in an attempt to identify virulence genes which are requisite to survival in vivo (Hong et al. (2000) Infect. Immun., 68:4102-4107; Zygmunt et al. (2006) Microb. Infect., 8:2849-2854). This technique involves a "negative" selection approach which relies on live animals to only identify mutations in those genes essential for host survival, and not immunogenic gene products. The method is also quite sensitive to experimental variables and to date has yielded limited information on molecular aspects of *Brucella* virulence. A less cumbersome and less artifactual approach is to utilize immune sera adsorbed with the in vitro-grown pathogen as a screening reagent for those gene products relevant to in vivo survival and pathogenesis. This technique is known as In vivo-Induced Antigen Technology, (IVIAT), and has been successfully used on bacterial pathogens to identify antigenic proteins expressed during infection (Handfield et al. (2000) Trends Microbiol., 8:336-339; Rollins et al. (2005) Cell. Microbiol., 7:1-9). Most recently, IVIAT has been applied to *Bacillus anthracis* to identify potential diagnostic, vaccine, and therapeutic candidates (Rollins et al. (2008) PLoS One 3:e1824). IVIAT has also been used with other facultative intracellular pathogens, such as *Mycobacterium tuberculosis* (Deb et al. (2002) Tuberculosis 82:175-182) and *Legionella pneumophila* (Chang et al. (2005) Infect. Immun., 73:4272-4280).

SUMMARY OF THE INVENTION

In accordance with the instant invention, methods of detecting a *Brucella* infection, particularly a *Brucella abortus* infection, in an animal are provided. In a particular embodiment, the method comprises a) obtaining a biological sample from the animal; and b) detecting the presence of at least one antibody immunologically specific for at least one *Brucella abortus* protein, wherein the presence of antibodies to the *Brucella abortus* protein indicates a *Brucella abortus* infection in the animal. In another embodiment, at least one *Brucella abortus* protein is selected from the examples hereinbelow, particularly Table 1, more particularly at least one *Brucella abortus* protein is malate dehydrogenase (Mdh), D15, or AfuA. In one embodiment, the methods allow for the differentiation between naturally infected and immunized animals and/or the differentiation based on *B. abortus* strains. In still another embodiment, compositions and kits are provided for the practice of the detection methods.

According to another aspect of the instant invention, methods of inhibiting a *Brucella* infection, particularly a *Brucella abortus* infection, in an animal are provided. In a particular embodiment, the method comprises administering to an animal at least one composition comprising at least one *Brucella abortus* protein, particularly one selected from the examples hereinbelow (particularly Table 1), and at least one pharmaceutically acceptable carrier. In one embodiment, at least one of the *Brucella abortus* proteins is malate dehydrogenase (Mdh), D15, or AfuA. In yet another embodiment, the method further comprises the administration of at least one other *Brucella abortus* vaccine and/or anti-microbial agent.

In accordance with yet another aspect, compositions comprising at least one *Brucella abortus* protein, particularly one selected from the examples hereinbelow (particularly Table 1), and at least one pharmaceutically acceptable carrier are provided. The compositions may be used to inhibit, treat, or prevent a *Brucella abortus* infection, e.g., as a vaccine against a *Brucella abortus* infection.

BRIEF DESCRIPTIONS OF THE DRAWING

FIG. 1 provides representative Western blots of recombinant AfuA, Mdh, and D15 against positive and negative serum samples. Molecular weights of the recombinant proteins are indicated in parentheses.

FIG. 2 provides an amino acid sequence of *B. abortus* D15 (GenBank Accession No. YP_413545; SEQ ID NO: 1).

FIG. 3 provides an amino acid sequence of *B. abortus* malate dehydrogenase (GenBank Accession No. YP_415266; SEQ ID NO: 2).

FIG. 4 provides an amino acid sequence of *B. abortus* AfuA (GenBank Accession No. YP_418727; SEQ ID NO: 3).

Figure 5:
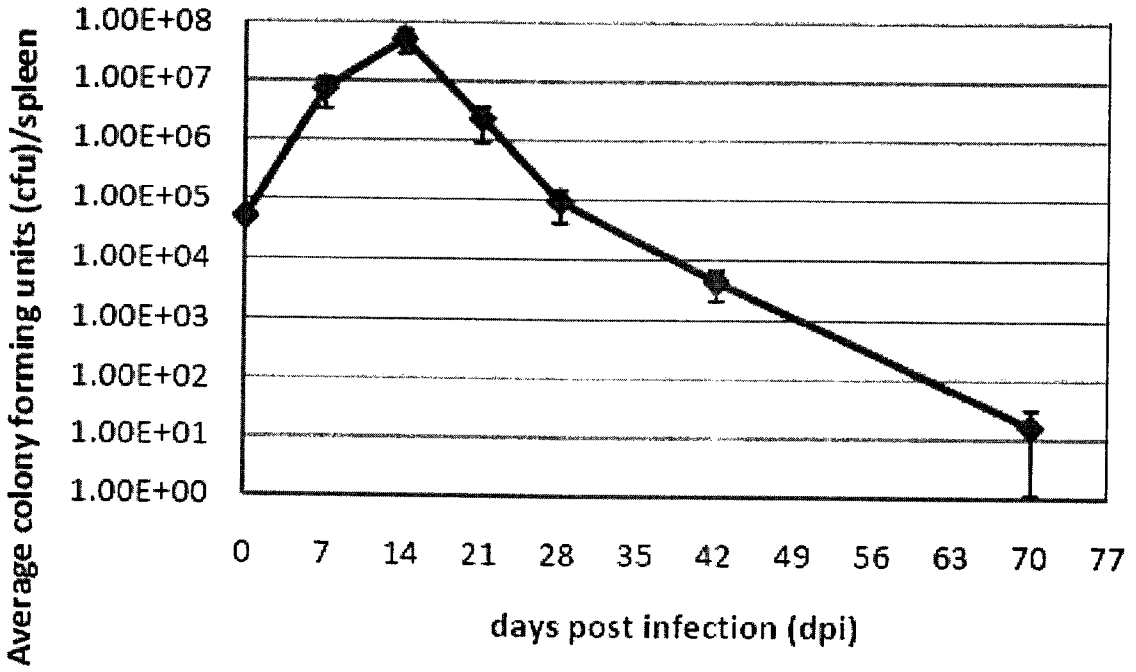

FIG. 5 provides a graph of *B. abortus* S19 load in mouse spleens 7, 14, 21, 28, 42, and 70 days post-infection with $5\times10^4$ *B. abortus* S19. Error bars represent one standard deviation.

Figure 6:
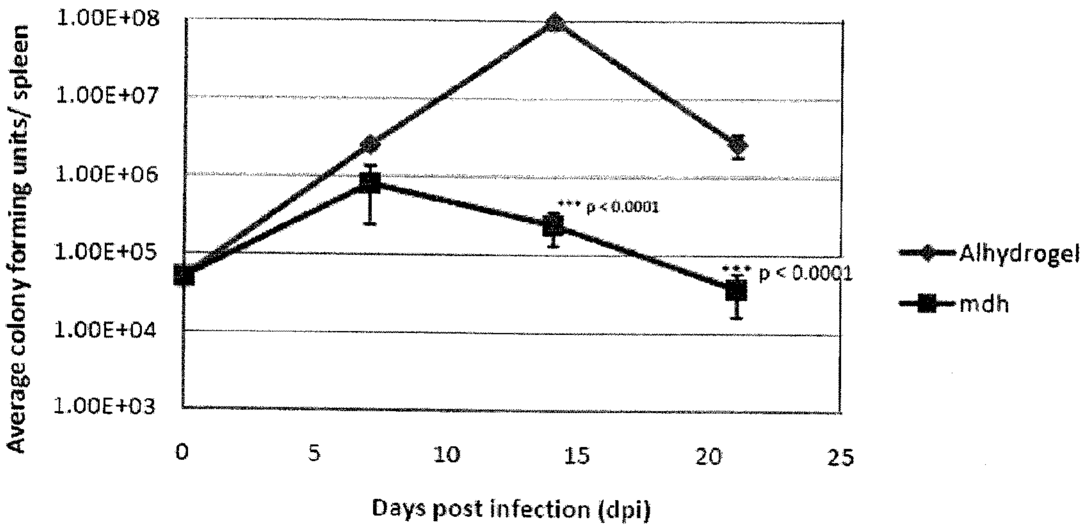

FIG. 6 provides a graph of *B. abortus* S19 load in mouse spleens 7, 14, and 21 days post-infection with $5\times10^4$ *B. abortus* S19 of mice immunized with mdh or control. Error bars represent one standard deviation. *** indicates $p<0.05$.

Figure 7:
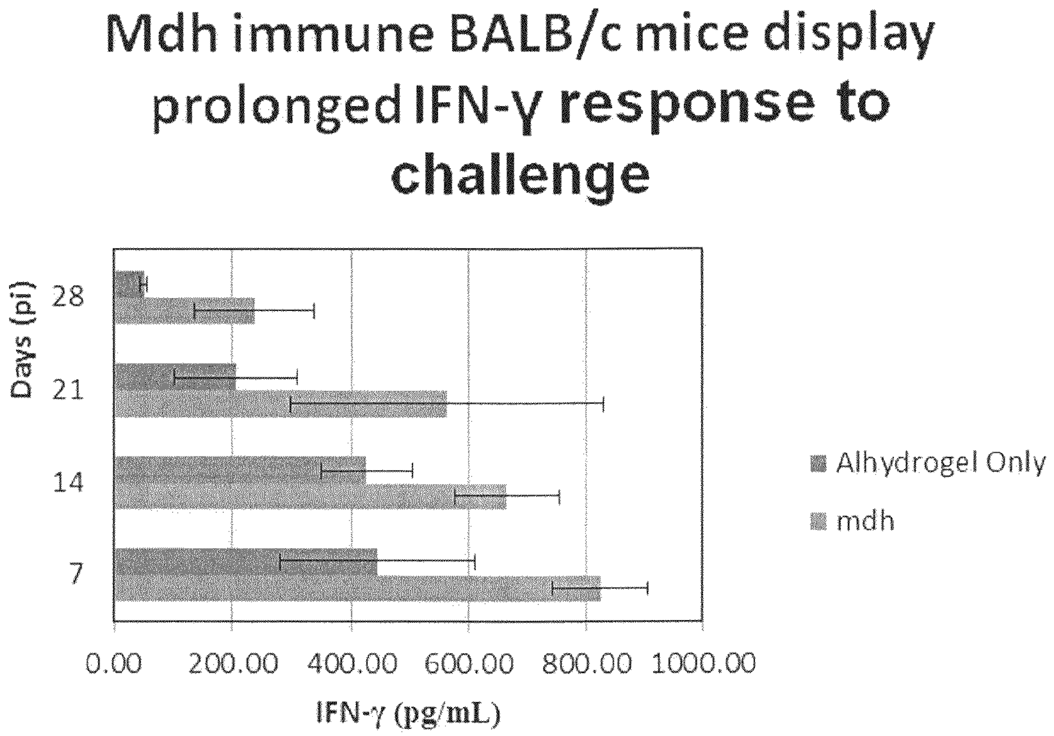

FIG. 7 provides a graph showing that Mdh immune BALB/c mice display prolonged IFN-γ response to challenge. Spleen homogenates from the five mice from each timepoint (7, 14, 21 and 28 dpi) sacrificed during the challenge studies were evaluated for IFN-γ production.

Figure 8:
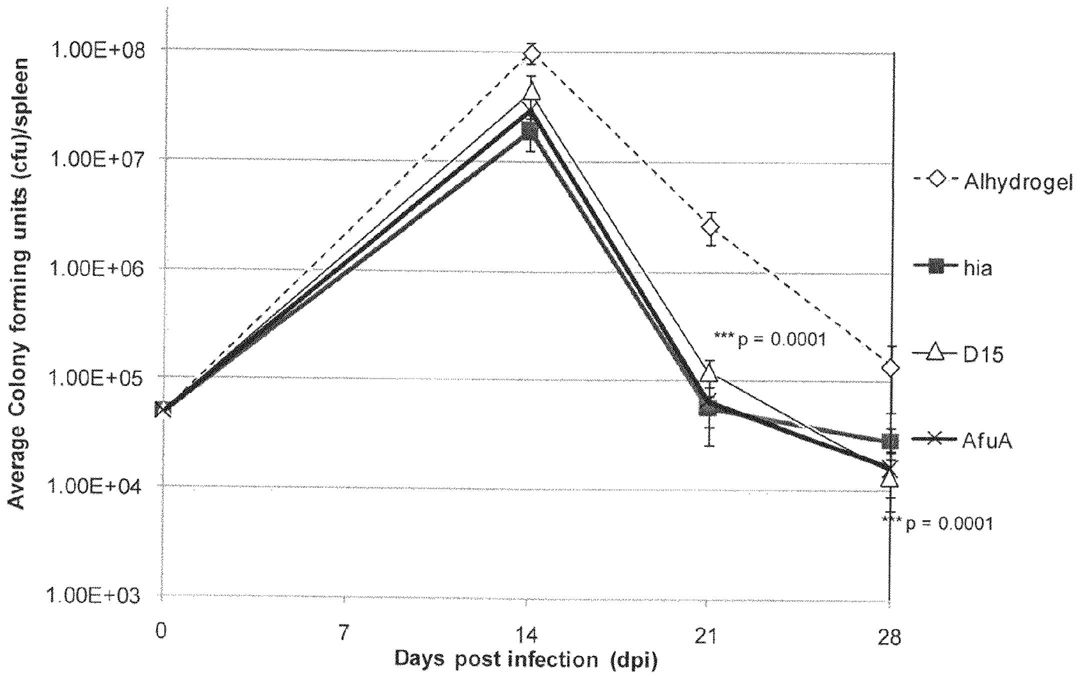

FIG. 8 provides a graph of *B. abortus* S19 load at three weeks post infection in BALB/c mice undergoing various treatments.

Figure 9:
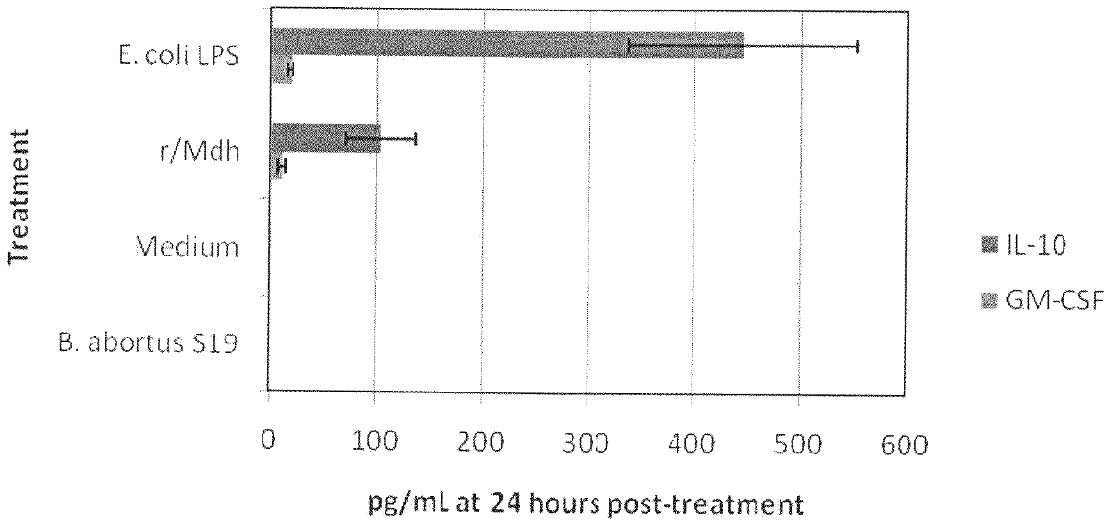

FIG. 9 provides a graph of IL-10 secretion from mouse macrophages exposed to various agents.

Figure 10:
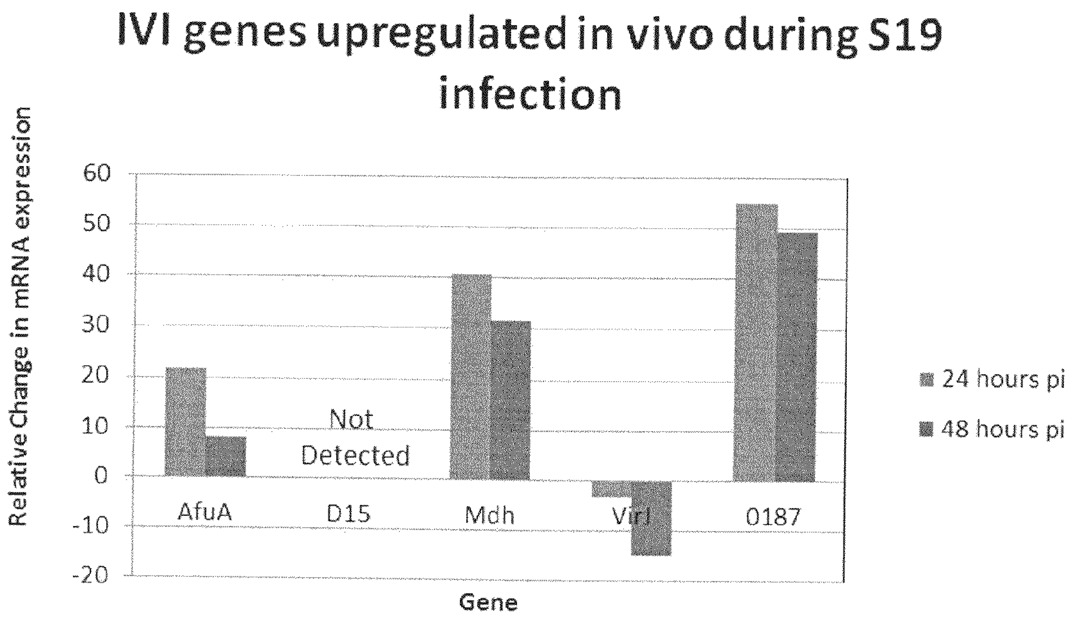

FIG. 10 provides a graph showing IVI genes upregulated in vivo during S19 infection. Average fold change of bacterial mRNA isolated from five mice infected with S19 at each time point compared to in vitro-grown *B. abortus* S19.

FIG. 11 provides an amino acid sequence of *B. abortus* Hia (GenBank Accession No. YP_220851.1; SEQ ID NO: 5).

DETAILED DESCRIPTION OF THE INVENTION

IVIAT is used herein to identify bacterial antigens relevant to the survival of *B. abortus* in elk and other mammals, with the anticipated outcome of determining what virulence effectors are important in this host-pathogen system, as well as to identify new diagnostic targets and/or sub-unit vaccine candidates that can be applied to different susceptible hosts.

Elk in the Greater Yellowstone Area are a major reservoir for brucellosis, which represents an obstacle to eradication of the disease in domestic livestock. Furthermore, immune responses to *Brucella abortus* infection in the wild host are not well-understood. In this regard, in vivo-induced antigen technology (IVIAT) was employed to identify novel *B. abortus* antigens expressed during infection in elk. Sera collected from sero-positive Wyoming elk were pooled and absorbed against in vitro-grown cultures of *B. abortus*. Approximately 35,000 *E. coli* clones, expressing *B. abortus* DNA, were then screened by colony immunoblot, yielding ten genes with immuno-reactive products, to include seven proteins secreted beyond the inner membrane. Three products—an outer membrane protein (D15), malate dehydrogenase (Mdh), and an ion transporter (AfuA)—were examined by Western blot against individual elk serum samples. Sero-reactivity was significantly more frequent for both Mdh and D15 in naturally infected animals, compared to vaccinated and uninfected elk, indicating that antibody to these two antigens is a predictor of natural infection. Cross-reactivity of all three proteins was next examined with serum samples from confirmed brucellosis-positive cattle. While variable patterns of reactivity were seen with the antigens, the sample group was equivalently reactive to AfuA and Mdh, compared to elk, indicating that these antigens are commonly expressed during infection in both hosts. Therefore, the application of IVIAT to *B. abortus* not only facilitates the identification of serologic markers for brucellosis in elk, but provides further insight into biological processes of the pathogen in different hosts.

With the application of the IVIAT gene discovery methodology to *B. abortus*, ten genes were identified which are expressed during infection and whose products are recognized by the cervid immune system. This outcome was the result of screening approximately 35,000 *E. coli* clones containing *Brucella* DNA with elk serum extensively adsorbed with in vitro-grown bacteria to remove antibodies to constitutively expressed proteins. Previous reports support the hypothesis that some of the genes are expressed during *Brucella* infection in several different hosts (Chirhart-Gilleland et al. (1998) Infect. Immun., 66:4000-4003; Ko et al. (2003) Clin. Microbiol. Rev., 16:65-78; Caro-Hernandez et al. (2007) Infect. Immun., 75:4050-4061), and that the application of IVIAT has further defined these antigens as being up-regulated in vivo. Unlike previous genes identified by STM (Hong et al. (2000) Infect. Immun., 68:4102-4107; Zygmunt et al. (2006) Microb. Infect., 8:2849-2854.), at least 30% of the loci identified through IVIAT are predicted to encode outer membrane proteins, which intuitively would be the candidates of choice for further examination as to their role in *Brucella* virulence. With this intent, the remaining antigens in this category, as well as the identified periplasmic proteins, can also be further characterized since their relevance to the survival of this microorganism in vivo cannot be discounted (Tang et al. (2005) J. Bacteriol., 187:6231-6237; Miranda et al. (2004) Infect. Immun., 72:1666-1676; Anderson et al. (2009) Infect Immun., 77:3466-74); Vines et al. (2005) J. Bacteriol., 187:3359-3368; Comerci et al. (2001) Cell Microbiol., 3:159-168; Roux et al. (2007) Cell Microbiol., 9:1851-1869).

In addition to detecting novel virulence genes, IVIAT has provided the means to identify *B. abortus* antigenic gene products as markers for infection. From the set of three recombinant IVIAT-identified proteins that were expressed and examined for sero-prevalence, a pattern of reactivity has emerged from serum collected from Wyoming elk. Antibody reactivity to two of the selected antigens, Mdh and D15, was shown to be a predictor of natural infection in this host. Moreover, an equivalent frequency of reactivity of at least one gene product, Mdh, was seen in immune domestic livestock, indicating that common biologic processes associated with this enzyme are utilized by *B. abortus* in different hosts. Accordingly, based on the observations in this study, the utility of these antigens extends to the diagnosis of brucellosis in other animals, such as domestic animals.

Although certain laboratory-based assays are capable of differentiating between *B. abortus* S19-vaccinated elk, and naturally infected animals (Van Houten et al. (2003) J. Wildl. Dis., 39:316-322.; Gall et al. (2001) J. Wildl. Dis., 37:110-118), both methods require operator training, are fairly labor intensive, and are not easily amendable to field application. The results provided herein demonstrate the potential for immobilized IVIAT-identified antigens to differentiate between vaccinated and naturally infected animals. This type of immune "footprinting" can also be useful for such differentiation in other susceptible hosts, and provide the basis of a new field deployable, rapid assay for the diagnosis of brucellosis in elk and/or domestic livestock. Such an assay, e.g., in a lateral flow device platform, has been developed for early detection and monitoring of other bacterial pathogens (Biagini et al. (2006) Clin. Vac. Immunol., 13:541-546). Furthermore, the cloning, expression and evaluation of additional in vivo-expressed genes may reveal additional patterns of humoral immunity which differentiate between infection by different *B. abortus* strains. Indeed, the IVIAT method can be repeated on other strains to identify further strain specific antigens.

Although *B. abortus* genes and their products identified through IVIAT can be further evaluated as to their exact role(s) in virulence, this approach can be used to identify antigens which are useful in generating protective immune responses in multiple hosts. The finding herein that two proteins were reactive with equivalent frequency in both cervid and bovine hosts (AfuA and Mdh) supports this conclusion.

I. Definitions

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g., chromatographic methods, agarose or polyacrylamide gel electrophoresis, HPLC analysis, and the like).

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25, 15-30, or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

Polymerase chain reaction (PCR) has been described in U.S. Pat. Nos. 4,683,195, 4,800,195, and 4,965,188, the entire disclosures of which are incorporated by reference herein.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$T_m=81.5° \text{ C.}+16.6 \text{ Log [Na+]}+0.41(\% \ G+C)-0.63(\% \text{ formamide})-600/\#\text{bp in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1×SSC and 0.5% SDS at 65° C. for 15 minutes.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% or more by weight of the given compound. Purity is measured by methods appropriate for the given compound (e.g. chromatographic methods, agarose or polyacrylamide gel electrophoresis, HPLC analysis, and the like).

The term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein and is generally found between exons.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

A "therapeutically effective amount" of a compound or a pharmaceutical composition refers to an amount effective to prevent, inhibit, treat, or lessen the symptoms of a particular disorder or disease. The treatment of a microbial infection (e.g., *B. abortus* infection) herein may refer to curing, relieving, and/or preventing the microbial infection, the symptom of it, or the predisposition towards it.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', $F(ab')_2$, F(v), scFv, $scFv_2$, scFv-Fc, minibody, diabody, tetrabody, single variable domain (e.g., variable heavy domain, variable light domain), and bispecific. Dabs can be composed of a single variable light or heavy chain domain. The instant invention also encompasses antibody mimetics such as Affibody® molecules (Affibody, Bromma, Sweden) and peptabodies (Terskikh et al. (1997) PNAS 94:1663-1668). Methods for producing antibodies (e.g., recombinantly) are well-known in the art.

With respect to antibodies, the term "immunologically specific" refers to antibodies that bind to one or more epitopes of a protein or compound of interest, but which do not substantially recognize and bind other molecules in a sample containing a mixed population of antigenic biological molecules. The term "specifically binds" refers to the binding of a polypeptide or compound of interest to a target polypeptide or compound while not substantially recognizing and binding other molecules in a sample containing a mixed population of biological molecules.

The phrases "affinity tag," "purification tag," and "epitope tag" may all refer to tags that can be used to effect the purification of a protein of interest. Purification/affinity/epitope tags are well known in the art (see Sambrook et al., 2001, Molecular Cloning, Cold Spring Harbor Laboratory) and include, but are not limited to: polyhistidine tags (e.g. 6×His), polyarginine tags, glutathione-S-transferase (GST), maltose binding protein (MBP), S-tag, influenza virus HA tag, thioredoxin, staphylococcal protein A tag, the FLAG™ epitope, AviTag™ epitope (for subsequent biotinylation), dihydrofolate reductase (DHFR), an antibody epitope (e.g., a sequence of amino acids recognized and bound by an antibody), the c-myc epitope, and heme binding peptides.

The phrase "solid support" refers to any solid surface including, without limitation, any chip (for example, silica-based, glass, or gold chip), glass slide, membrane, bead, solid particle (for example, agarose, sepharose, polystyrene or magnetic bead), column (or column material), test tube, lateral flow device, or microtiter dish.

As used herein, a "biological sample" refers to a sample of biological material obtained from a subject including a tissue, a tissue sample, a cell sample, and a biological fluid (e.g., blood, serum, or urine). Preferably, the biological sample is blood or serum.

II. Polypeptides

The *B. abortus* proteins of the present invention may be prepared in a variety of ways, according to known methods. In one embodiment, the B. aborted proteins are produced recombinantly. The *B. abortus* proteins may be purified from appropriate sources, e.g., bacterial or animal cultured cells or tissues, optionally transformed, by immunoaffinity purification. The availability of nucleic acid molecules encoding the *B. abortus* proteins also enables production of the protein using in vitro expression methods and cell-free expression systems known in the art. In vitro transcription and translation systems are commercially available, e.g., from Promega Biotech (Madison, Wis.) or Gibco-BRL (Gaithersburg, Md.).

Larger quantities of *B. abortus* proteins may be produced by expression in a suitable prokaryotic or eukaryotic system. For example, part or all of a DNA molecule encoding for a *B. abortus* proteins may be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

*B. abortus* proteins produced by gene expression in a recombinant prokaryotic or eukaryotic system may be purified according to methods known in the art. A commercially available expression/secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. The *B. abortus* proteins of the instant invention may be linked to at least one purification tag, as described herein. In a particular embodiment, the *B. abortus* protein is attached to a 6×His tag. In still another embodiment, the *B. abortus* protein is attached to the sequence Met-Ala-His-His-His-His-His-His-Val-Asp-Asp-Asp-Asp-Lys (SEQ ID NO: 4) on the amino terminus.

*B. abortus* proteins of the invention, prepared by the aforementioned methods, may be analyzed according to standard procedures. For example, such protein may be subjected to amino acid sequence analysis, according to known methods.

*B. abortus* proteins of the instant invention are provided in the examples hereinbelow, including those in Table 1 as well as PrpA, Hia, and MltE (particularly Hia). In a particular embodiment, the *B. abortus* proteins of the instant invention are selected from those provided in Table 1. In yet another embodiment, the *B. abortus* proteins is selected from the group consisting of D15, BA14K, Omp25d, malate dehydrogenase, AfuA, TolA, and VirJ. The *B. abortus* proteins may also be selected from the group consisting of Hia, D15, malate dehydrogenase, and AfuA. In still another embodiment, the *B. abortus* proteins are selected from the group consisting of D15, malate dehydrogenase, and AfuA. FIGS. 2-4 provide amino acid sequence of *B. abortus* D15, *B. abortus* malate dehydrogenase, and *B. abortus* AfuA, respectively. The amino acid sequences of the other proteins may be obtained through their GenBank ID numbers (e.g., at www.ncbi.nlm.nih.gov/genbank/). The amino acid sequence of the *B. abortus* proteins of the instant invention may have at least 75%, 80%, 85%, 90%, 95%, 97%, 99%, or 100% homology with the provided sequence (e.g., SEQ ID NOs: 1-3 and 5 or those provided in GenBank), particularly at least 90% or 95% homology.

The instant invention also encompasses antibodies immunologically specific for the *B. abortus* proteins of the instant invention.

III. Nucleic Acid Molecules

Nucleic acid molecules encoding the *B. abortus* proteins of the invention may be prepared by any method known in the art such as (1) synthesis from appropriate nucleotide triphosphates or (2) isolation and/or amplification from biological sources. The availability of nucleotide sequence information enables preparation of an isolated nucleic acid molecule of the invention by oligonucleotide synthesis. Indeed, knowledge of the amino sequence is sufficient to determine an encoding nucleic acid molecule. Synthetic oligonucleotides may be prepared by the phosphoramidite method employed in the Applied Biosystems 38A DNA Synthesizer or similar devices. The resultant construct may be purified according to methods known in the art, such as gel electrophoresis or high performance liquid chromatography (HPLC).

Nucleic acid sequences encoding the *B. abortus* proteins of the invention may be isolated from appropriate biological sources using methods known in the art. In one embodiment, a cDNA clone of the *B. abortus* proteins is isolated from a cDNA expression library and modified, if necessary, to create the *B. abortus* proteins of the instant invention. In an alternative embodiment, utilizing the sequence information provided by the cDNA sequence, genomic clones encoding *B. abortus* proteins may be isolated.

Nucleic acids of the present invention may be maintained in any convenient vector, particularly an expression vector. Different promoters may be utilized to drive expression of the nucleic acid sequences based on the cell in which it is to be expressed. Antibiotic resistance markers are also included in these vectors to enable selection of transformed cells. *B. abortus* protein encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention.

Also encompassed in the scope of the present invention are oligonucleotide probes which specifically hybridize with the *B. abortus* protein nucleic acid molecules of the invention. Primers capable of specifically amplifying *B. abortus* protein encoding nucleic acids described herein are also contemplated herein. Such oligonucleotides are useful as probes and primers for detecting, isolating or amplifying *B. abortus* protein encoding nucleic acids.

It will be appreciated by persons skilled in the art that variants (e.g., allelic variants) of the *B. abortus* protein sequences exist and may be taken into account when designing and/or utilizing oligonucleotides of the invention. Accordingly, it is within the scope of the present invention to encompass such variants, with respect to the *B. abortus* protein sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a population. The usage of different wobble codons and genetic polymorphisms which give rise to conservative or neutral amino acid substitutions in the encoded protein are examples of such variants. Such variants would not demonstrate substantially altered *B. abortus* protein activity or protein levels.

IV. Compositions and Methods

The present invention also encompasses compositions comprising at least one *B. abortus* protein of the instant invention and at least one pharmaceutically acceptable carrier. Such a pharmaceutical composition may be administered, in a therapeutically effective amount (e.g., an amount sufficient to elicit an immune response (e.g., as a vaccine)), to a patient in need thereof. The pharmaceutical compositions of the present invention can be administered by any suitable route, for example, by injection (e.g., parenteral, intramuscular, intravenous, or intraperitoneal administration), by oral, pulmonary, subcutaneous, nasal, topical, or other modes of administration such as controlled release devices. In general, pharmaceutical compositions and carriers of the present invention comprise, among other things, pharmaceutically acceptable diluents, preservatives, stabilizing agents, solubilizers, emulsifiers, adjuvants and/or carriers. Such compositions can include diluents of various buffer content (e.g., saline, Tris HCl, acetate, phosphate), pH and ionic strength; and additives such as detergents and solubilizing agents (e.g., Tween 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. Exemplary pharmaceutical compositions and carriers are provided, e.g., in "Remington's Pharmaceutical Sciences" by E. W. Martin (Mack Pub. Co., Easton, Pa.) and "Remington: The Science And Practice Of Pharmacy" by Alfonso R. Gennaro (Lippincott Williams & Wilkins, 2005) which are herein incorporated by reference. The pharmaceutical composition of the present invention can be prepared, for example, in liquid form, or can be in dried powder form (e.g., lyophilized).

The present invention also encompasses methods for preventing, inhibiting, and/or treating bacterial infections, particularly *B. abortus* infections. In a particular embodiment, the compositions of the instant invention are administered as a vaccine. The pharmaceutical compositions of the instant invention can be administered to an animal, in particular a mammal, in order to treat/inhibit/prevent a *B. abortus* infection. Examples of animals to be treated include, without limitation, domestic livestock, cervid, bovine, elk, cattle, and bison. The pharmaceutical compositions of the instant invention may also comprise at least one other anti-microbial agent (e.g., antibiotic), particularly at least one other anti-*B. abortus* compound/agent/vaccine. The additional anti-*B. abortus* compound may also be administered in separate composition from the *B. abortus* proteins of the instant invention. The compositions may be administered at the same time or at different times (e.g., sequentially). While the above methods describe the inhibition of a *B. abortus* infection, the methods can also be employed more generally to inhibit/treat/prevent brucellosis as well as reduce/eliminate the symptoms associated therewith. In a particular embodiment of the instant invention, the composition to be administered to the animal comprises at least one, particularly at least two or three, proteins from Table 1. In still another embodiment, the composition comprises at least one, at least two, or all of D15, mdh, and AfuA.

The instant invention also encompasses methods for detecting a *B. abortus* infection in an animal (e.g., diagnosing) and/or detecting brucellosis in an animal. In a particular embodiment, the method comprises 1) obtaining a biological sample from an animal and 2) detecting the presence of at least one *B. abortus* protein of the instant invention and/or an antibody specific for a *B. abortus* protein of the instant invention, wherein the presence of a *B. abortus* protein of the instant invention and/or antibody specific for a *B. abortus* protein of the instant invention is indicative of a *B. abortus* infection in the animal. While it is preferred to screen for antibodies to the proteins of the instant invention, the instant invention also encompasses methods wherein nucleic acid molecules which encode the *B. abortus* protein of the instant invention are screened for (e.g., by using nucleic acid probes) or the *B. abortus* protein of the instant invention are screened for themselves. In a particular embodiment, the biological sample obtained from the animal is blood or serum. In still another embodiment, the methods comprise screening for at least one antibody specific for at least one *B. abortus* protein selected from Table 1. In still another embodiment, methods comprise screening for at least one antibody specific for at least one, at least two, or all of D15, mdh, and AfuA (particularly at least mdh or at least D15 and mdh).

In a particular embodiment, the methods of the instant invention allow for the detection of a natural *B. abortus* infection (e.g., as opposed to a vaccinated (e.g., *B. abortus* S19) host). In this embodiment, it is preferred that the methods comprise screening for D15 and/or mdh (e.g., antibodies specific for D15 and/or mdh).

The composition(s) of the instant invention may also be contained within a kit. The instant invention also encompasses kits comprising a solid support (e.g., one suitable for a lateral flow device) comprising at least one *B. abortus* protein of the instant invention attached to the surface. In a particular embodiment, the *B. abortus* protein(s) comprise at least one, at least two, or all of D15, mdh, and AfuA (particularly at least mdh or at least D15 and mdh). The kits may further comprise buffers and detection reagents (e.g., labeled (e.g., radio-labeled or fluorescent) secondary antibodies (e.g., specific to host antibodies)) suitable for detecting the binding of an antibody to the protein(s) immobilized on the solid support.

The following examples describe illustrative methods of practicing the instant invention and are not intended to limit the scope of the invention in any way.

EXAMPLE 1

Materials and Methods

Library Construction

*Brucella abortus* RB51 was kindly provided by Colorado Serum Company (Denver, Colo.). Although RB51 is attenuated in vivo, this vaccine strain is isogenic to the wild-type strain 2308 (Schurig et al. (1991) Vet. Microbiol., 28:171-188), possessing lesions in LPS biosynthesis loci (Vemulapalli et al. (2000) Infect. Immun., 68:3927-3932). It was therefore deemed suitable for use in the construction of a *Brucella* gene expression library. RB51 was grown at 37° C. for 48 hours in brain heart infusion broth. Genomic DNA was extracted using the Wizard® Genomic DNA Purification Kit (Promega, Madison, Wis.), and partially digested by the restriction enzyme Sau3A for 1 hour at 37° C. DNA fragments were then ligated into the pET-30abc system overnight (EMD Biosciences, La Jolla, Calif.). The *B. abortus* DNA was subsequently transformed into *E. coli* BL-21 cells (Stratagene, La Jolla, Calif.) for library plasmid amplification, and the DNA re-transformed into BL-21[DE3] cells for expression.

Serum Processing

Serum samples from infected elk were obtained from the Wyoming Game and Fish Department's Wildlife Disease Laboratory, a federally approved brucellosis testing facility. Samples were evaluated using the card, standard plate, rivanol, fluorescence polarization assay, and cELISA (to distinguish between S19-immunity and field strain infection), and defined as "positive" if reactions occurred in three of four tests, per federal guidelines for *Cervidae* (USDA, 2003).

Five serum samples were pooled to reduce animal-to-animal variability in reactivity to specific antigens. The sample pool was then filter-sterilized and mixed with in vitro-grown whole cells and lysates of *B. abortus* RB51, as well as *E. coli* BL-21[DE3] to remove in vitro-specific antibodies, as described by others (Deb et al. (2002) Tuberculosis 82:175-182; Chang et al. (2005) Infect. Immun., 73:4272-4280). The adsorption process was repeated 3-5 times, and reactivity to in vitro-grown bacteria was monitored by immunoblot to ensure removal of antibody to constitutively expressed antigens. Additionally, to rule out the possibility of false positives among any reactive clones, pooled elk serum was further adsorbed with whole cells and lysates of in vitro growth *B. abortus* 2308, and used to re-probe clones (by colony lift) and/or their recombinant products (by slot blot) reactive with the adsorbed serum used in the initial screening.

Immuno-Screening

After 5 hours of incubation at 37° C., *E. coli* BL-21[DE3] colonies were lifted from the plates using Protran® nitrocellulose membrane disks (Whatman, Kent, UK), inverted and placed on fresh LB agar plates containing antibiotic and 1 mM IPTG. After incubation at 30° C. overnight, the membranes were exposed to chloroform vapor for 15 minutes and allowed to dry. Once dry, the membranes were treated with 5% skim milk powder and 0.05% Tween-20 (blotto) for 1 hour, rinsed for 5 minutes with PBS (+0.05% Tween® 20), and incubated with absorbed sera at a 1:500 dilution in blotto for 2 hours. After incubation, the membranes were washed 5 times with PBS, then incubated with a 1:5000 dilution of Alkaline Phosphatase-Conjugated, Protein G (Rockland, Gilbertsville, Pa.) in blotto for 1 hour. Afterwards, the membrane was washed 3 times for 5 minutes with PBS and incubated for 5 minutes with a stabilized substrate (Promega, Madison, Wis.). After color development, membranes were rinsed with deionized water for 5 minutes.

Gene Identification

Following rinsing and drying steps, the membranes were matched to the master plate and appropriate colonies selected and isolated. Suspect reactive colonies were grown in broth culture and serial diluted onto new plates. Serologic screening was repeated again and DNA extracted from positive clones purified using the Small Plasmid Prep Kit (Qiagen, Valencia, Calif.) and sequenced from the vector-specified T7 promoter (University of Wyoming Nucleic Acid Exploration Facility). The sequence was then compared against the NCBI Entrez database's *B. abortus* strain 9-941 and 2308 genomes for DNA/protein alignments. Subcellular localization of putative IVIAT-identified products was determined using the PSORTb v 2.0 algorithm (Gardy et al. (2005) Bioinformatics 21:617-623).

Expression Plasmid, Construction, Recombinant Protein Expression, and Purification Selected in vivo-expressed genes, encoding Mdh, D15, and AfuA, were amplified in their entirety from the *B. abortus* RB51 genome by PCR using PfuUltra™ Master Mix (Stratagene, La Jolla, Calif.) inserted into the pET-46 Ek/LIC system (EMD Biosciences, La Jolla, Calif.), and transformed into *E. coli* NovaBlue cells (EMD Biosciences, La Jolla, Calif.). The recombinant constructs were then purified and the insert sequence confirmed by PCR and sequencing. Selected plasmid constructs were re-transformed into *E. coli* Rosetta-2[DE3] cells (EMD Biosciences, La Jolla, Calif.) and induced to express under 0.5 mM IPTG. Verification of expression of recombinant products was confirmed by total crude protein resolution on SDS-PAGE followed by Western blot analysis using a His-tagged monoclonal antibody (EMD Biosciences, La Jolla, Calif.). Ten milliliters of IPTG-induced cultures of recombinant *E. coli* strains were treated with BugBuster® HT (EMD Biosciences, La Jolla, Calif.) and soluble fractions containing recombinant histidine-tagged fusion proteins purified by the HisMag™ Purification Kit (EMD Biosciences, La Jolla, Calif.). The proteins were run on a SDS-PAGE gel to confirm purity and quantified by spectral absorption at 280 nm.

Sero-Reactivity of Selected IVIAT-Identified Proteins

Sera from individual elk confirmed positive for infection with wild-type *B. abortus* or immunized with *B. abortus* S19 were probed against recombinant Mdh, D15, and AfuA. Purified proteins were first electrophoresed on Tris-Tricine preparative acrylamide gels (Jule, Inc., Biotechnologies, Milford, Conn.), transferred via semi-dry electroblotting to nitrocellulose membranes, and treated as similarly described for the library immunoblotting procedure. Blot strips with 5-10 mg of immobilized protein were exposed to 1 ml of a 1:10 dilution of test serum for 1 hour at room temperature and washed prior to addition of the secondary antibody. Colorometric reactions were stopped after 10 minutes, and reactivity scored as either positive or negative. Cross-reactivity of Mdh, D15, and AfuA in *B. abortus* confirmed positive cattle was assessed with bovine serum samples kindly provided by Dr. Will Reeves, ABADRL, USDA.

Statistical Review

The two-tailed Fisher's Exact test was applied to the immunoblot results to determine if differences observed in reactivity of any given individual antigen between animal groups (infected, immunized, naive) were significant. A chi-square analysis was used on the cumulative data.

Results

*Brucella abortus* IVI Gene Identification

The *B. abortus* RB51 library in *E. coli*, represented by a total of approximately 35,000 clones, was probed with extensively adsorbed, pooled immune elk serum. Ten colonies confirmed as immuno-reactive were isolated and their *Brucella*-specific inserts sequenced and compared against the genomes for *B. abortus* strains 9-941 and 2308 in NBCI's GenBank. All ten loci possessed identical alleles among both strains, with the exception of one (virJ) which was divergent in the first 85 amino acids of the predicted product. Additionally, the products from all ten clones remained equivalently reactive to pooled, adsorbed serum which had been re-adsorbed with whole cells and lysates of laboratory-grown strain 2308, suggesting that the in vitro expression profiles for the ten gene products identified in the original screen are the same between 2308 and its isogenic rough derivative. All but two of the predicted proteins fell into a functional category from either the NCBI, COG (Clusters of Orthologous Groups [of proteins]) or the cd (conserved domain) databases (Table 1). These categories included: protein secretion, cell envelope biogenesis, inorganic ion transport, and metabolism. Two genes, however, predicted products of unknown function. Four of the proteins were also determined to be unique to the Rhizobiales order (Table 1). The 10 gene products were subsequently grouped by their predicted cellular localization. At least seven of the antigenic proteins possess primary and secondary structure which indicates secretion beyond the inner membrane (Gardy et al. (2005) Bioinformatics 21:617-623).

TABLE 1

*Brucella abortus* IVI gene products identified by screening with absorbed immune elk sera.

| *Brucella abortus* gene product ID[a] | COG or CDD# identification[b] | Putative function | Predicted cellular localization[c] |
|---|---|---|---|
| BAB1_0045 | "D15" domain COG0729 | Protein processing[d] | Outer Membrane |
| BAB1_0187[f] | BA14K domain: lipoprotein, pfam07886 | Cell envelope stability[e] | Outer Membrane |
| BAB2_0115[f] | Omp25d; Type-V domain; COG3637 | Auto-secreted surface protein[g] | Outer Membrane |
| BAB1_1927 | Mdh: malate dehydrogenase, cd01339 | Gluconeo-genesis[h] | Periplasm |
| BAB2_0539 | AfuA domain; COG1840 | Iron ABC transporter component[i] | Periplasm |
| BAB1_1710 | TolA domain | Cell envelope Stability[j] | Periplasm |
| BAB2_0654 | VirJ domain COG3946 | Type-IV secretion[k] | Periplasm |
| BAB1_0819[f] | Lipoprotein | Unknown | Unknown |
| BAB1_1282 | Hydrolase; cd00312 | Unknown | Unknown |
| BAB2_0959[f] | RfbX domain: O-antigen flippase, COG2244 | LPS biosynthesis[l] | Inner Membrane |

[a]entrez GenBank.
[b]NCBI, Clusters of Orthologous Groups [of proteins]; conserved domain databases.
[c]PSORTb v 2.0.
[d]Manning et al. (Microb. Pathog. (1998) 25: 11-21), Robert et al. (PLoS Biol. (2006) 4: e377).
[e]Chirhart-Gilleland et al. (Infect. Immun. (1998) 66: 4000-4003).
[f]Unique to *Rhizobiales* Order.
[g]Caro-Hernandez et al. (Infect. Immun. (2007) 75: 4050-4061).
[h]Tang et al. (J. Bacteriol. (2005) 187: 6231-6237), Miranda et al. (Infect. Immun. (2004) 72: 1666-1676).
[i]Anderson et al. (Infect Immun. (2009) 77: 3466-74).
[j]Vines et al. (J. Bacteriol. (2005) 187: 3359-3368).
[k]Comerci et al. (Cell Microbiol. (2001) 3: 159-168), Roux et al. (Cell Microbiol. (2007) 9: 1851-1869).
[l]Liu et al. (J. Bacteriol. (1996) 178: 2102-2107).

Serologic Analysis of Selected Gene Products Identified Through IVIAT

To explore the utility of a diagnostic application for these antigens in elk, recombinant proteins from three selected loci, D15 (1_0045), Mdh (1_1927), and AfuA (2_0539), were purified to homogeneity, electrophoresed, electro-blotted, and probed with serum dilutions from groups of 5-9 uninfected, vaccine-immune (S19), and naturally infected elk. FIG. 1 shows 12 representative reactive and non-reactive blots of the three recombinant proteins using a 1:10 dilution of individual serum samples. The serologic survey results of all elk are summarized in Table 2. While no single antigen was uniquely reactive between any of the animal groups, collectively, a significantly higher frequency of reactivity in the naturally infected group was evident (p=0.001). An analysis of individual antigens showed that reactivity was significantly more frequent for both Mdh (p=0.007) and D15 (p=0.001) in the group of naturally infected animals, compared to S19-immunized animals and naïve animals. Although a higher frequency of reactivity was seen with AfuA in naturally infected animals, the difference was not statistically significant compared to S19-immunized elk. To determine if these proteins were expressed and immunogenic in a domestic host previously diagnosed with brucellosis, 8 confirmed sero-positive cattle serum samples were evaluated by Western blot at the same dilution. As shown in Table 3, the frequency of reactivity of AfuA and Mdh was equivalent to that seen in the naturally infected elk samples tested. Reactivity to D15, however was significantly less frequent in sero-positive cattle compared with naturally infected elk (p=0.05).

TABLE 2

Frequency of Elk immune responses to selected IVTAT-identified *Brucella* antigens.

| Animal Group | AfuA | Mdh | D15 | Cumulative reactivity |
|---|---|---|---|---|
| Natural Infection | 8/9 | 7/9[a] | 8/9[a] | 23/27[a] |
| S19-immunized | 4/6 | 0/6 | 0/6 | 4/18 |
| NEG | 0/5 | 0/5 | 0/5 | 0/15 |
| Naturally infected vs. S19 | | p = 0.007 | p = 0.001 | p < 0.001 |

[a]Significantly higher frequency of sero-reactivity.

TABLE 3

Cross-reactivity of selected *Brucella* IVIAT-identified antigens with *B. abortus* sero-reactive cattle.

| Animal Group | AfuA | Mdh | D15 | Cumulative reactivity |
|---|---|---|---|---|
| POS | 6/8[a] | 7/8[a] | 3/8 | 16/24[a] |
| NEG | 0/8 | 0/8 | 0/8 | 0/24 |
| POS vs. NEG | p = 0.007 | p = 0.001 | | p < 0.001 |
| POS cattle vs. naturally infected elk | | | p = 0.05 | |

[a]Significantly higher frequency of sero-reactivity.

EXAMPLE 2

Brucellosis caused by *Brucella abortus* is a significant disease in wildlife and domestic animal populations in Wyoming and across the globe. Infection can result in abortion, and/or persistence of the pathogen. Recent studies show that 40% of pregnant heifers vaccinated RB51 and challenged with fully virulent *B. abortus* will abort (Poester et al. (2006) Vaccine 24:5327-5334). RB51 is also ineffective in eliciting protective immunity to brucellosis in cervids (Olsen et al. (2006) Clin. Vaccine Immunol., 13:1098-11103). In 2008, Wyoming suffered another outbreak of brucellosis in a cattle herd, highlighting the state's need for an alternative to RB51 for both cattle and cervid populations. Application of in vivo induced antigen technology (IVIAT) to brucellosis has facilitated the identification of numerous genes up-regulated in vivo, whose products are immunogenic in cervids.

Furthermore, several *Brucella* spp. have been classed as category B threat list agents with the potential for use as bioterrorism weapons. Efforts to develop an effective, stable, and non-reactogenic vaccine against brucellosis have been ongoing in several laboratories, and the use of a live, attenuated platform has become the established benchmark through the use of the *B. abortus* rough strain RB51 (Schurig et al. (2002) Vet. Microbiol., 90:479-496). Although moderate efficacy against *Brucella*-induced fetal abortions in domestic livestock (cattle) has been reported (Elzer et al. (1998) Am. J. Vet. Res., 59:1575-1578), acceptable levels of protection following immunization with RB51 has yet to be demonstrated in wildlife such as elk (Cook et al. (2002) J. Wildl. Dis., 38:18-26), and in the case of bison, results have been conflicting in terms of the vaccine's reactogenicity (Elzer et al. (1998) J. Wildl. Dis., 34:825-829; Olsen et al. (1999) Am. J. Vet. Res., 60:905-8; Palmer et al. (1996) Vet. Pathol., 33:682-691). The exact nature of the attenuation of RB51 is also unclear, although it's rough LPS phenotype is due to at least one lesion in O-side chain biosynthesis loci (Schurig et al. (2002) Vet. Microbiol., 90:479-496). A more systematic approach to the induction of active protective immunity against brucellosis has been undertaken by some laboratories through the development of subunit vaccines (Al-Mariri et al. (2001) Infect. Immun., 69:4816-4822; He et al. (2002) Infect. Immun., 70:2535-2543; Kaushik et al. (2010) Vet. Res. Comm., 34:119-132; Pasquevich et al. (2009) Infect. Immun., 77:436-445; Delpino et al. (2007) Vaccine 25:6721-6729; Cassataro et al. (2007) Clin. Vaccine Immunol., 14:869-874). To date, the degree of success in protecting with such vaccines depends on the ability of the candidate to drive immunity towards a Th1-type response, emphasizing the need to identify and characterize *Brucella* antigens which present T-cell epitopes to the host (Ko et al. (2003) Clin. Microbiol. Rev., 16:65-78). Despite the efforts to identify components for a next-generation subunit vaccine, formulations using recombinant *Brucella* antigens have not been thoroughly assessed for immunogenicity/efficacy. The discovery of additional *Brucella* virulence factors thus may facilitate the development of a more efficacious, less reactogenic, acellular product that may either be used as a stand-alone vaccine or used to augment primary immunization with the existing live, attenuated platform. As an example of the latter strategy, enhanced efficacy has been reported by over-expressing *Brucella* superoxide dismutase (SOD) in RB51 or complementing the strain's rough LPS phenotype with the O-side chain biosynthesis locus, wboA (Vemulapalli et al. (2004) Vet. Microb., 102:237-245).

As described hereinabove, the gene discovery methodology, known as in vivo-induced antigen technology (IVIAT), has been applied to identify *B. abortus* virulence genes up-regulated during infection in elk (*Cervis elaphus*), and as a result ten loci with gene products potentially important to survival of the pathogen in this host have been identified. Furthermore, the conserved nature of most of these gene products has led to the conclusion that they also may be requisite virulence effectors in other *Brucella* susceptible hosts. As a preliminary approach to confirming this hypothesis, five of these in vivo-induced (IVI) products have been selected for further characterization in a surrogate murine model for *B. abortus* colonization: a conserved outer membrane protein, D15; a gluconeogenic enzyme, malate dehydrogenase (Mdh); a periplasmic component of an ABC transport system, AfuA; a component of the Type-IV secretion system (TOSS) VirJ; and a lipoprotein of unknown function BAB1_0187 (referred to as 0187). Three additional conserved genes based on high amino acid sequence similarity with loci identified through *Yersinia pestis* IVIAT and previous reports of a role in *Brucella* pathogenesis (Andrews et al. (2010) Vector-Borne and Zoonotic Dis., 10(8):749-756; Spera et al. (2006) Proc. Nat. Acad. Sci., 103:16514-16519) were also targeted: a proline epimerase (PrpA; BAB1_1800 (strain 2308)), an auto-secreting (Type-V) surface antigen (Hia; BruAb1_0072 (9-941)), the other encoding a soluble lytic transglycosylase (MltE; BruAb1_0661 (9-941)).

Materials and Methods

Bacterial Strains and Growth Conditions

*Brucella abortus* S19, was kindly provided by the Colorado Serum Company (Denver, Colo.), and was used exclusively for this study in the mouse colonization/infection model. Brain-heart infusion broth cultures were typically grown overnight at 37° C., serially diluted after three washes in sterile PBS, followed by plating to determine a viable cell count correlate with optical density at 600 nm.

In Vivo Gene Expression, RNA Extraction, and RT-PCR

Ten BALB/c mice were infected with $1\times10^7$ cfu of *B. abortus* S19 i.p. Mice were splenectomized and tissues stored in RNAlater® (Ambion, Austin, Tex.). Tissues were homogenized and RNA isolated with the RiboPure™-Bacteria Kit (Ambion, Austin, Tex.). Isolated RNA was transcribed to cDNA using RETROscript® (Ambion, Austin, Tex.) and cDNA targets amplified by PfuTurbo® DNA Polymerase (Stratagene, La Jolla, Calif.) in a one-step reaction. Amplification of a segment of the 16S subunit of *B. Abortus* S19 was used as a positive control; negative controls were included for each gene and contained all the reaction components except reverse transcriptase. In addition a negative control was employed which lacked RNA template to confirm the absence of DNA contamination in the reaction. Concentration of PCR product in gel bands was assessed using Quantity One 4.6 (Bio-rad, Hercules, Calif.).

Plasmid Construction, Recombinant Protein Expression, and Purification

Selected IVI genes were amplified in their entirety from the *B. abortus* RB51 genome by PCR, using PfuUltra Master Mix (Stratagene, La Jolla, Calif.), inserted into the pET-46 Ek/LIC system (EMD Biosciences, La Jolla, Calif.), and transformed into *E. coli* NovaBlue cells (EMD Biosciences, La Jolla, Calif.). The recombinant plasmid constructs were then purified and the insert sequence confirmed by PCR and sequencing. The recombinant plasmids were re-transformed into *E. coli* Rosetta-2[DE3] cells (EMD Biosciences, La Jolla, Calif.) and induced to express under 0.5 mM IPTG at 30° C. Verification of expression of recombinant products was performed by total crude protein resolution on SDS-PAGE followed by Western blot analysis using a His-tagged Monoclonal antibody (EMD Biosciences, La Jolla, Calif.). Ten mls of 0.5 mM IPTG-induced cultures of recombinant *E. coli* strains were treated with BugBuster® HT (EMD Biosciences, La Jolla, Calif.) and soluble (AfuA, Mdh, MltE, 0187) and insoluble (D15, VirJ, Hia) fractions containing recombinant histidine-tagged fusion proteins purified by the HisMag™ Purification Kit (EMD Biosciences, La Jolla, Calif.). Insoluble fractions containing D15, VirJ, and Hia were purified under 8M Urea, followed by dialysis against PBS. The proteins were run on a SDS-PAGE gel to confirm purity and quantified by spectral absorption at 280 nm and BCA Lowry (Pierce Chemical).

Subunit Vaccine Preparation

Purified proteins were mixed with a 1:7 dilution of aluminum hydroxide adjuvant (Alhydrogel; Superfos, Denmark) in PBS and adsorbed overnight at 4° C. at a concentration of 150 μg/mL.

Animal Studies

All animals utilized in this study were cared for according to strict adherence to the Policies and Regulations established by the US Public Health Service "Humane Care and Use of Laboratory Animals" and an approved animal protocol from the University of Wyoming Institutional Animal Care and Use Committee (IACUC) (DHHS Assurance #A3216-1). Animals were euthanized by the AVMA approved method of cervical dislocation.

Ten to 30 six-week old, female BALB/c mice received 30 μg of recombinant protein subcutaneously in 200 μL of adjuvant at one site. Additional control mice were treated with adjuvant only in the same manner. Immunization regimen consisted of a prime and two boosts, 21 days apart. Retro-orbital bleeds were performed to assess antibody titers by Western blot. Animals were challenged with $5\times10^4$ organisms of *B. abortus* S19 occurred at 14 days after the second boost. Five mice from each group were sacrificed at specific time points. Spleens were removed, weighed, homogenized, used to determine whole organ bacterial load following serial dilution of the homogenates in 1× Sterile PBS and plating on blood agar. The remaining homogenates were stored at −40° C. for cytokine analysis.

Cytokine Analysis

Supernatants from spleen homogenates were used in QuantiKine® ELISA Assays (R&D Systems, Minneapolis, Minn.) to quantify IL-12p70, IL-4, and IFN-γ cytokine levels in the spleen.

Statistics

All statistical analysis was completed in the software package SAS 9.1 Enterprise (SAS Corporation, Cary, N.C.). ANOVA was used to compare means of groups and Least Significant Difference (LSD) was used to determine mean separations between the groups. $\alpha=0.05$; p values are listed in text.

Results

S19 Infection Kinetics

To establish the colonization kinetics of *B. abortus* S19 in BALB/c mice, thirty naive animals were infected with S19 at $5\times10^4$ CFU and five animals sacrificed at 7, 14, 21, 28, 42, and 70 days post-infection. As shown in FIG. 5, bacterial loads in spleens peaked in two weeks at $8\times10^7$ CFU before gradually declining to $6\times10^3$ CFU in 6 weeks. These observations were consistent with a previous report of S19 colonization kinetics in mice (Montaraz et al. (1986) Infect. Immun., 53:245-251), however in the instant study, at 10 weeks post infection, organisms were still able to be cultured from spleens in 60% of the animals. Also, S19-induced splenomegaly in mice correlated with the bacterial load at specific time points, peaking between 14 and 21 days post-infection, and declining by day 28 (Table 4).

TABLE 4

Splenomegaly peaks at two weeks post infection and declines by four weeks in naive mice infected with *B. abortus* S19.

| Days post infection (dpi) | Weight (mg) | SD |
|---|---|---|
| 7 | 454 | +/−120 |
| 14 | 864 | +/−110 |
| 21 | 690 | +/−134 |
| 28 | 245 | +/−72 |

TABLE 4-continued

Splenomegaly peaks at two weeks post infection and declines by four weeks in naive mice infected with *B. abortus* S19.

| Days post infection (dpi) | Weight (mg) | SD |
|---|---|---|
| 42 | 172 | +/−58 |
| 70 | 163 | +/−64 |

S19 Challenge after Vaccination with Recombinant IVI Products

As seen in FIG. 6, the vaccination with recombinant Mdh reduced *B. abortus* S19 colonization in the spleen of BALB/c mice. 15 mice were immunized with mdh. 5 mice were sacrificed at 7, 14, and 21 days post-infection and bacterial loads in the spleen were determined. Alhydrogel® only animals represent pooled data from all vaccination studies.

In another experiment, thirty mice were vaccinated with purified Mdh, MltE, or adjuvant-only. After hyper-immunization with the recombinant proteins, the sera was assessed for antibody. End-point titers from mice immunized with the recombinant protein ranged from a 1:1000 to 1:5000. Serum from mice receiving alhydrogel alone was non-reactive against any of the proteins. After challenge, bacterial loads in the spleens were determined at 7, 14, 21, and 28 days post-infection. As shown in Table 5, mice vaccinated with Mdh showed a markedly significant decrease in bacterial colonization at 14 dpi providing 2.75 log units of clearance and 2 log units of clearance at 21 days post-infection compared to adjuvant-only treated animals ($p<0.001$). Bacterial loads measured in MltE-immunized mice were no different than the adjuvant-only controls. Mdh-immunized animals also displayed extended splenomegaly which remained elevated relative to the adjuvant-only animals at 28 days post-infection (Table 5). By 42 days, the Mdh-immunized animals had completely cleared the infection, while S19 was still cultured from spleens of the adjuvant-only mice at the same time point.

TABLE 5

Reduction of bacterial load and more rapid clearance in a murine colonization model by immunization with recombinant *B. abortus* Mdh.

| Time, Post-infection (days) | Adjuvant Only | Mdh | p value | Log protection |
|---|---|---|---|---|
| 0 | — | — | — | — |
| 7 | $2.51\times10^6$ (+/−$3.34\times10^5$) | $8.05\times10^5$ (+/−$5.62\times10^5$) | <0.05 | 0.55 |
| 14 | $9.94\times10^7$ (+/−$2.17\times10^7$) | $2.43\times10^5$ (+/−$1.12\times10^5$) | <0.001 | 2.75 |
| 21 | $2.64\times10^6$ (+/−$8.57\times10^5$) | $3.73\times10^4$ (+/−$2.08\times10^4$) | <0.001 | 2.09 |
| 28 | $1.38\times10^5$ (+/−$8.37\times10^4$) | $1.29\times10^4$ (+/−$1.00\times10^4$) | <0.05 | 1.09 |

In another experiment, fifteen mice each received alhydrogel only, AfuA, Hia or D15 recombinant proteins adsorbed to the adjuvant. Mice were primed and boosted twice, and serum was collected to assay for antibody titers. Reactivity of the immune sera to all three antigens was comparable to that of Mdh immunized mice. The animals were challenged as before and bacterial loads in the spleens assessed at 14, 21, and 28 days post-infection. As shown in Table 6, in contrast to Mdh, there was no significant difference at two weeks between the adjuvant-only and antigen-immunized animal groups, however at three weeks post-infection all three experimental groups differed significantly from the adjuvant only group with D15 providing the most pronounced effect of 1.41 log units of clearance ($p<0.001$). As observed with Mdh-immunized animals, splenomegaly remained consistently elevated in all test groups at 28 days post-infection relative to the adjuvant-only control animals (Table 7).

TABLE 6

Reduction of bacterial load in a murine colonization model by immunization with recombinant *B. abortus* AfuA, D15, or Hia.

| Time (days) Post-infection | Adjuvant Only | AfuA | D15 | Hia | p value |
|---|---|---|---|---|---|
| 0 | — | — | — | — | |
| 7 | | ND | ND | ND | |
| 14 | $9.94 \times 10^7$ (+/−$2.17 \times 10^7$) | $2.89 \times 10^7$ (+/−$1.78 \times 10^7$) | $4.40 \times 10^7$ (+/−$2.23 \times 10^7$) | $1.88 \times 10^7$ (+/−$7.02 \times 10^6$) | |
| 21 | $2.64 \times 10^6$ (+/−$8.57 \times 10^5$) | $6.53 \times 10^4$ (+/−$5.38 \times 10^4$) | $1.23 \times 10^5$ (+/−$8.05 \times 10^4$) | $4.20 \times 10^4$ (+/−$2.81 \times 10^4$) | <0.001 (D15) |
| 28 | $1.38 \times 10^5$ (+/−$8.37 \times 10^4$) | $1.59 \times 10^4$ (+/−$9.31 \times 10^3$) | $1.50 \times 10^4$ (+/−$9.08 \times 10^3$) | $2.89 \times 10^4$ (+/−$1.27 \times 10^4$) | <0.05 (Hia) |

TABLE 7

Immunization with recombinant proteins induce prolong splenomegaly in BALB/c mice.

| Mouse Group | 14 days (mg) SD | 21 days (mg) SD | 28 days (mg) SD |
|---|---|---|---|
| AfuA | 710 (+/−199.1) | 530 (+/−95.9) | 352 (+/−77.2) |
| hia | 648.8 (+/−274.7) | 464 (+/−188.5) | 532 (+/−122.6) |
| D15 | 588 (+/−152.1) | 550 (+/−296.3) | 332 (+/−122.6) |
| Mdh | 557 (+/−223.3) | 671 (+/−313.2) | 335 (+/−44.2) |
| VirJ | 685 (+/−375) | 536 (+/−336) | ND |
| 187 | 646 (+/−271) | 945 (+/−92) | ND |
| PrpA | 747 (+/−129) | 570 (+/−183) | ND |
| Alhydrogel | 658 (+/−96.2) | 772 (+/−265.3) | 172 (+/−62.2) |

Another iteration was then conducted to evaluate VirJ, 0187, and PrpA. Following the same methods as above, antibody titers were determined to be >1:5000 (VirJ, PrpA and 0187). Mice were challenged with S19 and splenic colony counts were performed as described previously at 14 and 21 days post-infection. No significant difference was found between adjuvant-only animals and those receiving any of the three antigens (Table 8), although all immune animals displayed some degree of splenomegaly (Table 7).

TABLE 8

Immunization with VirJ, PrpA, or 0187 have no effect on reduction of colonization by S19.

| Time, Post-infection (days) | Adjuvant Only | VirJ | PrpA | 0187 | Log Protection |
|---|---|---|---|---|---|
| 0 | — | | — | | |
| 7 | $5.65 \times 10^5$ (+/−$1.79 \times 10^5$) | ND | ND | ND | |
| 14 | $2.41 \times 10^7$ (+/−$4.46 \times 10^6$) | $3.16 \times 10^7$ (+/−$5.20 \times 10^6$) | $1.12 \times 10^7$ (+/−$5.78 \times 10^6$) | $3.39 \times 10^7$ (+/−$3.06 \times 10^6$) | N/A |
| 21 | $1.50 \times 10^6$ (+/−$3.80 \times 10^5$) | $1.15 \times 10^6$ (+/−$5.14 \times 10^5$) | $1.19 \times 10^7$ (+/−$3.31 \times 10^6$) | $2.41 \times 10^6$ (+/−$6.05 \times 10^5$) | N/A |

Mouse Cytokine Response to Challenge with S19

Levels of IL-12p70, IL-4 and IFN-γ in the splenic homogenates were quantified from the five selected animal groups immunized with antigens which had an effect on bacterial load and/or clearance rate. No detectable IL-12p70 or IL-4 groups immunized with AfuA, Hia, D15, or adjuvant alone was observed. IL-4 was, however, detected in Mdh-vaccinated mice, although at low levels.

IFN-γ was next assessed in vaccinated mice after challenge. 5 spleen tissue homogenates from each group and timepoint were assayed by ELISA. As shown in FIG. 7, at all sampling times, mice vaccinated with Mdh showed significantly higher levels of this cytokine ($p<0.05$), compared to the mice receiving alhydrogel alone (or AfuA or D15). By 21 and 28 days post-infection, IFN-γ levels among all groups had declined with the exception of the Mdh immune group, in which IFN-γ remained significantly elevated ($p<0.05$; FIG. 7). Additionally, BALB/c mice vaccinated with Mdh show increased splenomegaly. Indeed, at one week, Mdh vaccinated spleens were 717.6±209.2 mg whereas as MltE spleens were 460.6±181.0 mg and Alhydrogel® mice were 506.8±160.4 mg. At two weeks, Mdh vaccinated spleens were 1057.8±43.5 mg whereas as MltE spleens were 986.2±102.9 mg and Alhydrogel® mice were 878.2±52.5 mg.

As seen in FIG. 8, immunization with recombinant proteins promotes faster clearance of *B. abortus* S19 at three weeks post infection in BALB/c mice.

As seen in FIG. 9, recombinant malate dehydrogenase induces IL-10 secretion from mouse macrophages. $2\times10^5$ J774 mouse macrophages were treated with recombinant forms of 30 μg of hia, D15, AfuA, mdh, and 40 μg of *E. coli* LPS, and *B. abortus* S19 (10 MOI). Culture supernatants at 24 hours were removed and assayed for GM-CSF and IL-10 cytokine production.

In addition to the above, vaccination studies in mice with D15 and AfuA have shown that each of these proteins is capable of eliciting an immune response in mice challenged with *B. abortus* S19.

In Vivo Assessment of IVI Gene Up-Regulation During S19 Infection in Mice

"Short-unique" regions of selected IVI gene targets identified by IVIAT from elk infected with wild-type *B. abortus* were selected for construction of RT-PCR primers. Ten BALB/c mice were subsequently infected with S19, five of which were splenectomised at 24 and 48 hours post-infection, and bacterial mRNA isolated. Additionally, S19 was grown to mid-log phase in vitro and mRNA extracted for comparison. Analysis showed up-regulation during both 24 and 48 hours post-infection of afuA, mdh, and 0187 (FIG. 10). In contrast, D15 mRNA was not detected in either the in vitro or in vivo samples, even after performing several different nested RT-PCR reactions. Hia transcript was, as expected, expressed at equivalent levels in vitro and during infection.

Certain mouse strains have been shown to be highly sensitive to *B. abortus* and have been used to study *B. abortus* pathogenesis and evaluate vaccine candidates for the past two decades (Montaraz et al. (1986) Infect. Immun., 53: 245-251; Cheers, C. (1984) Dev. Biol. Standard, 56:237-246; Bosseray, N. (1992) Dev. Biol. Standard, 79:121-128; Bosseray et al. (1990) Vaccine 8:462-468; Baldwin C L, Winter A J (1994) Immunol. Ser., 60:363-380; Tobias et al. (1993) Vet. Pathol., 30:119-129). Furthermore, studies with S19 in pregnant BALB/c mice reported an identical pathology, placentitis and septic fetal death, as with wild-type *B. abortus* infection, further supporting the applicability of this model to the simulation of disease in other host species (Tobias et al. (1993) Vet. Pathol., 30:119-129; Tobias et al. (1992) Res. Vet. Sci., 53:179-183). The benefit of using S19 instead of wild-type *B. abortus* is reduced cost and safety, since BSL-3 small animal containment facilities are not required.

Vaccination with purified *B. abortus* Mdh resulted in significantly reduced colonization and more rapid clearance of S19 in the BALB/c mouse. Interestingly, Mdh was the only recombinant protein of the five antigens examined which facilitated some level of clearance that elicited a significant IFN-γ response, a cytokine critical for the activation of macrophages and a requisite for controlling *Brucella* infections (Baldwin et al. (2006) Crit. Rev. Immunol., 26:407-442). It is therefore likely that prolonged elevated levels of IFN-γ in mice vaccinated with Mdh contribute to the reduction in the colonization by S19 in these immune animals. The nature of Mdh-induced immune-mediated enhanced clearance is unclear at present, however, it is possible that an auxiliary virulence function of the enzyme may be neutralized by a robust immune response directed toward it. The presence of IL-4 and absence of IL-12 also suggest that mice vaccinated with Mdh induce a Th2-biased response leading to clearance immunity mediated by antibody. In fact, a search for putative T- and B-cell epitopes across the amino acid sequence of the protein revealed only the latter. This hypothesis may seem contrary to the traditional notion that only a Th1-biased response can reduce intracellular bacterial load in the *Brucella*-infected host. Indeed, previous experiments with other facultative intracellular pathogens such as *Yersinia pestis* have demonstrated that antibody alone can confer protection against challenge (Sofer-Podesta et al. (2009) Infect. Immun., 77:1561-1568). In the case of *B. abortus*, an "optimized" Th2 response might also contribute significantly to clearing infection.

Although, immunity to AfuA and D15 failed to elicit more rapid clearance of S19, bacterial loads were significantly reduced in animals immunized with either of these two proteins. In contrast to AfuA and Mdh, D15 expression was not evident early in S19 colonization, thus D15 may be relevant at a later stage of infection in the mouse. Curiously, as described hereinabove, an antibody to Mdh and D15 was not detected in S19-immunized elk, indicating that both proteins may be regulated differently in cervids.

Hia was not identified as an IVI gene initially, and consistent with this finding, was subsequently was found to be constitutively expressed based on an mRNA analysis. The selection of this gene product was based on similar homology to *Y. pestis* protein and previous reports in the literature of involvement as a virulence factor (Alamuri Pet al. (2010) Infect. Immun., 78:4882-4894). This type-V auto-secreted antigen, induced a greater level of extended splenomegaly compared to the other recombinant proteins, including Mdh. However, the increased inflammation did not correlate with heightened production of IFN-γ. This observation indicates that immunity to Hia may increase the inflammatory response during infection by mechanisms not related to IFN-γ, such as TNF-α or IL-1. Although immunization with Hia reduced bacterial load in the mouse model comparable to D15 and AfuA, it failed to induce more rapid clearance.

As with MltE, 0187, PrpA, and VirJ failed to reduce bacterial load and/or alter clearance kinetics compared to adjuvant-only controls. 0187 is a putative lipoprotein that shares significant homology with the well characterized BA14K protein. Previous studies have demonstrated that BA14K was able to induce a Th1 response and induce IL-12 secretion (Chirhart-Gilleland et al. (1998) Infect. Immun., 66:4000-4003). 0187 was not expressed from *B. abortus* as a full length protein but it was stably expressed as a truncated form shortened by 27 amino acids from the N-terminus. It is possible that this truncation could have resulted in conformation changes leading to an inability to induce clearance immunity.

PrpA, which encodes a proline epimerase was described as a B-cell polyclonal activator and inducer of IL-10 (Spera et al. (2006) Proc. Nat. Acad. Sci., 103:16514-16519), suggested that immunity to this protein may promote clearance in the model based on the pivotal role IL-10 plays in *Brucella* pathogenesis (Baldwin et al. (2006) Crit. Rev. Immunol., 26:407-442; Fernandes et al. (1995) Infect. Immun., 63:1130-1133). Mice immunized with PrpA during early infection actually had splenic counts higher than animals sham-immunized with adjuvant alone. It is possible that a secondary exposure to PrpA results in host immune dysregulation early during the course of infection.

The data above strongly suggested that the Type-IV secretion system (T4SS) accessory protein, VirJ, is up-regulated during wild type *B. abortus* infection in elk. Animals immunized with S19 however did not generate a humoral response to the protein, which suggests a difference in the way this secreton is utilized by S19 in cervids. Consistent with this finding, in the S19 murine colonization model, VirJ appears to be slightly down-regulated at least during early stages of infection. A BLAST analysis upstream and downstream of VirJ revealed no differences between S19, 2308 or 9-941 (Wyoming strain) genome sequences, suggesting the involvement of a distal regulatory element(s) in controlling expression in S19. The function of VirJ, as assessed in other pathogens, is suspected to be as a periplasmic chaperone responsible for assisting substrates in associating with a "pusher" pilus before translocation through the T4SS, typically thought to be required for full virulence in this pathogen (Zhong et al. (2009) Microbiol., 155:3392-3402). In this regard, VirJ may be studied in a *B. abortus* 2308 challenge model.

Data from the model system is in agreement with that previously published for S19 colonization in BALB/c mice, and also demonstrated for the first time that mice remain colonized with S19 at ten weeks post infection. The vaccination efforts with a single recombinant protein, Mdh, coincide with previously reported data on mice vaccinated with RB51 in terms of the subsequent cytokine responses post-challenge (Wang et al. (2010) FEMS Microbiol. Letters, 303:92-100). IFN-γ levels peak between 6 and 7 days then begin to slowly decline, albeit remaining sustained for weeks (Wang et al. (2010) FEMS Microbiol. Letters, 303:92-100). RB51 vaccinates also lack significant production IL-12p70 or high levels of IL-4 upon challenge (Wang et al. (2010) FEMS Microbiol. Letters, 303:92-100). Notably, BALB/c mice tend to be more biased towards humoral responses (Schurig et al. (2002) Vet. Microbiol., 90:479-496; Baldwin et al. (2006) Crit. Rev. Immunol., 26:407-442; Wang et al. (2010) FEMS Microbiol. Letters, 303:92-100). As predicted, the S19 data shows that a pro-inflammatory response is suppressed in naïve animals and behaves similarly to strain 2308 in this respect (Baldwin et al. (2006) Crit. Rev. Immunol., 26:407-442). This indicates that a shift in cytokine production levels is important in providing a more efficacious immune response to brucellosis.

Taken together, these data indicate the potential for use of the gluconeogenic enzyme, malate dehydrogenase, as a recombinant subunit vaccine candidate for brucellosis. AfuA and D15 also represent subunit vaccine candidates, particularly when used together and/or in combination with Mdh. Collectively, the in vivo data gathered from the S19 murine colonization model indicate that vaccination with at least three of the IVIAT antigens conferred an enhanced ability of the host to respond to infection, establishing the utility of this methodology for the identification of potential vaccine candidates against brucellosis.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A composition comprising isolated *Brucella abortus* malate dehydrogenase, at least one additional isolated *Brucella abortus* protein, and at least one pharmaceutically acceptable carrier, wherein said *Brucella abortus* malate dehydrogenase comprises SEQ ID NO: 2.

2. The composition of claim 1, wherein said additional *Brucella abortus* protein(s) is selected from the group consisting of Hia, D15, and AfuA.

3. The composition of claim 1, wherein said composition comprises *Brucella abortus* malate dehydrogenase and D15.

4. The composition of claim 1, wherein said composition comprises *Brucella abortus* malate dehydrogenase, D15, and AfuA.

5. The composition of claim 1, wherein said additional *Brucella abortus* protein(s) is selected from the group consisting of D15, BA14K, Omp25d, AfuA, TolA, VirJ, BAB1_0819, BAB1_1282, PrpA, Hia, MltE, and RfbX.

6. The composition of claim 2, wherein said D15 comprises an amino acid sequence having at least 90% homology with SEQ ID NO: 1; wherein said AfuA comprises an amino acid sequence having at least 90% homology with SEQ ID NO: 3; and wherein said Hia comprises an amino acid sequence having at least 90% homology with SEQ ID NO: 5.

7. A method of inhibiting a *Brucella abortus* infection in an animal, said method comprising administering a composition of claim 1 to said animal.

8. The method of claim 7, further comprising the administration of at least one other *Brucella abortus* vaccine.

* * * * *